(12) United States Patent
Look et al.

(10) Patent No.: US 10,561,440 B2
(45) Date of Patent: Feb. 18, 2020

(54) SYSTEMS AND METHODS FOR MANIPULATING MEDICAL DEVICES

(71) Applicant: VESATEK, LLC, Irvine, CA (US)

(72) Inventors: David M. Look, Newport Beach, CA (US); Bradley S. Culbert, Tustin, CA (US)

(73) Assignee: Vesatek, LLC, Irvine, CA (US)

( * ) Notice: Subject to any disclaimer, the term of this patent is extended or adjusted under 35 U.S.C. 154(b) by 383 days.

(21) Appl. No.: 15/256,488

(22) Filed: Sep. 2, 2016

(65) Prior Publication Data

US 2017/0065396 A1 Mar. 9, 2017

Related U.S. Application Data

(60) Provisional application No. 62/214,192, filed on Sep. 3, 2015, provisional application No. 62/286,429, filed on Jan. 24, 2016.

(51) Int. Cl.
*A61B 17/3207* (2006.01)
*A61B 17/3203* (2006.01)

(52) U.S. Cl.
CPC ............ *A61B 17/320758* (2013.01); *A61B 17/32037* (2013.01)

(58) Field of Classification Search
CPC ........ A61B 17/3207; A61B 17/320725; A61B 17/32075; A61B 17/320758;
(Continued)

(56) References Cited

U.S. PATENT DOCUMENTS 1,114,268 A 10/1914 Kells
1,148,093 A 7/1915 Kells
(Continued)

FOREIGN PATENT DOCUMENTS

DE 3715418 A1 11/1987
EP 0709110 A1 5/1996
(Continued)

OTHER PUBLICATIONS

"Comparison of Dimensions and Aspiration Rate of the Pronto V3, Pronto LP, Export XT, Export AP, Fetch, Xtract, Diver C.E. and QuickCat Catheter", Vascular Solutions, Inc., downloaded from internet Oct. 22, 2014.
(Continued)

*Primary Examiner* — Dianne Dornbusch
(74) *Attorney, Agent, or Firm* — Blair Walker IP Services, LLC

(57) ABSTRACT

A method for treating a patient having thrombus includes providing a manipulation device including a housing configured to be supported by the hand of a user and having a distal and proximal end, a drive system disposed within the housing, and configured to rotate a rotation member, an engagement member coupled to the rotation member and configured to be removably coupled to an elongate medical device, an activation member carried by the housing such that it can be operated by at least a portion of the hand of the user when the housing is supported by the hand of the user, the drive system configured to apply motive force to the engagement member, securing an elongate member to the engagement member, introducing at least the distal end of the elongate member into a blood vessel adjacent a thrombus, operating the activation member to cause at least some rotation of the rotation member, which in turn causes at least some rotation of the distal end of the elongate member at or near the thrombus, and aspirating at least some of the thrombus with an aspiration catheter.

19 Claims, 23 Drawing Sheets

(58) Field of Classification Search
CPC ...... A61B 17/3203; A61B 2017/32032; A61B 2017/32035; A61B 2217/005; A61B 2217/002; A61B 2217/007
See application file for complete search history.

(56) References Cited

U.S. PATENT DOCUMENTS

| | | |
|---|---|---|
| 2,804,075 A | 8/1957 | Borden |
| 3,429,313 A | 2/1969 | Romanelli |
| 3,631,847 A | 1/1972 | Hobbs, II |
| 3,693,613 A | 9/1972 | Kelman |
| 3,707,967 A | 1/1973 | Kitrilakis et al. |
| 3,748,435 A | 7/1973 | Reynolds |
| 3,847,140 A | 11/1974 | Ayella |
| 3,916,892 A | 11/1975 | Latham, Jr. |
| 3,930,505 A | 1/1976 | Wallach |
| 3,955,573 A | 5/1976 | Hansen et al. |
| 4,030,503 A | 6/1977 | Clark, III |
| 4,299,221 A | 11/1981 | Phillips et al. |
| 4,465,470 A | 8/1984 | Keiman |
| 4,574,812 A | 3/1986 | Arkans |
| 4,638,539 A | 1/1987 | Palmer |
| 4,690,672 A | 9/1987 | Veltrup |
| 4,700,705 A | 10/1987 | Kensey et al. |
| 4,728,319 A | 3/1988 | Masch |
| 4,747,821 A | 5/1988 | Kensey et al. |
| 4,790,813 A | 12/1988 | Kensey |
| 4,832,685 A | 5/1989 | Haines |
| 4,842,579 A | 6/1989 | Shiber |
| 4,854,325 A | 8/1989 | Stevens |
| 4,857,046 A | 8/1989 | Stevens et al. |
| 4,883,458 A | 11/1989 | Shiber |
| 4,883,467 A | 11/1989 | Franetzki et al. |
| 4,886,490 A | 12/1989 | Shiber |
| 4,894,051 A | 1/1990 | Shiber |
| 4,898,574 A | 2/1990 | Uchiyama et al. |
| 4,957,482 A | 9/1990 | Shiber |
| 4,979,939 A | 12/1990 | Shiber |
| 4,998,919 A | 3/1991 | Schnepp-Pesch |
| 5,002,553 A | 3/1991 | Shiber |
| 5,007,896 A | 4/1991 | Shiber |
| 5,011,488 A * | 4/1991 | Ginsburg ............... A61B 17/22 604/104 |
| 5,024,651 A | 6/1991 | Shiber |
| 5,055,109 A | 10/1991 | Gould et al. |
| 5,057,098 A | 10/1991 | Zelman |
| 5,064,428 A | 11/1991 | Cope et al. |
| 5,073,164 A | 12/1991 | Hollister et al. |
| 5,073,168 A | 12/1991 | Danforth |
| 5,074,841 A | 12/1991 | Ademovic et al. |
| 5,078,722 A | 1/1992 | Stevens |
| 5,125,893 A | 6/1992 | Dryden |
| 5,135,482 A | 8/1992 | Neracher |
| 5,135,531 A | 8/1992 | Shiber |
| 5,158,564 A | 10/1992 | Schnepp-Pesch et al. |
| 5,195,954 A | 3/1993 | Schnepp-Pesch et al. |
| 5,197,951 A | 3/1993 | Mahurkar et al. |
| 5,234,407 A | 8/1993 | Teirstein et al. |
| 5,243,997 A | 9/1993 | Uflacker et al. |
| 5,248,297 A | 9/1993 | Takase |
| 5,261,877 A | 11/1993 | Fine et al. |
| 5,284,486 A * | 2/1994 | Kotula ........... A61B 17/320758 606/159 |
| 5,290,247 A | 3/1994 | Crittenden |
| 5,306,244 A | 4/1994 | Shiber |
| 5,312,427 A | 5/1994 | Shturman |
| 5,318,518 A | 6/1994 | Plechinger et al. |
| 5,318,529 A | 6/1994 | Kontos |
| 5,320,604 A | 6/1994 | Walker et al. |
| 5,322,504 A | 6/1994 | Doherty et al. |
| 5,324,263 A | 6/1994 | Kraus et al. |
| 5,325,868 A | 7/1994 | Kimmelstiel |
| 5,327,906 A | 7/1994 | Fideler |
| 5,334,211 A | 8/1994 | Shiber |
| 5,342,293 A | 8/1994 | Zanger |
| 5,342,306 A | 8/1994 | Don Michael |
| 5,368,555 A | 11/1994 | Sussman et al. |
| 5,385,562 A | 1/1995 | Adams et al. |
| 5,389,072 A | 2/1995 | Imran |
| 5,392,778 A | 2/1995 | Horzewski |
| 5,395,315 A | 3/1995 | Griep |
| 5,403,274 A | 4/1995 | Cannon |
| 5,413,561 A | 5/1995 | Fischell et al. |
| 5,419,772 A | 5/1995 | Teitz et al. |
| 5,421,826 A | 6/1995 | Crocker et al. |
| 5,443,078 A | 8/1995 | Uflacker |
| 5,443,443 A | 8/1995 | Shiber |
| 5,486,183 A | 1/1996 | Middleman et al. |
| 5,490,837 A | 2/1996 | Blaeser et al. |
| 5,496,267 A | 3/1996 | Drasler et al. |
| 5,507,738 A | 4/1996 | Ciervo |
| 5,524,180 A | 6/1996 | Wang et al. |
| 5,524,635 A | 6/1996 | Uflacker et al. |
| 5,527,274 A | 6/1996 | Zakko |
| 5,536,242 A | 7/1996 | Willard et al. |
| 5,569,275 A * | 10/1996 | Kotula ........... A61B 17/320758 606/159 |
| 5,606,968 A | 3/1997 | Mang |
| 5,624,394 A | 4/1997 | Barnitz et al. |
| 5,634,475 A | 6/1997 | Wolvek |
| 5,647,847 A | 7/1997 | Lafontaine et al. |
| 5,653,696 A | 8/1997 | Shiber |
| 5,660,180 A | 8/1997 | Malinowski et al. |
| 5,695,507 A * | 12/1997 | Auth ............... A61B 17/22031 604/22 |
| 5,709,661 A | 1/1998 | Van Egmond et al. |
| 5,713,849 A | 2/1998 | Bosma et al. |
| 5,713,851 A | 2/1998 | Boudewijn et al. |
| 5,730,717 A | 3/1998 | Gelbfish |
| 5,735,535 A | 4/1998 | McCombs et al. |
| 5,766,191 A | 6/1998 | Trerotola |
| 5,772,674 A | 6/1998 | Nakhjavan |
| 5,785,685 A | 7/1998 | Kugler et al. |
| 5,795,322 A | 8/1998 | Boudewijn |
| 5,827,229 A | 10/1998 | Auth et al. |
| 5,827,243 A | 10/1998 | Palestrant |
| 5,843,022 A | 12/1998 | Willard et al. |
| 5,843,051 A | 12/1998 | Adams et al. |
| 5,855,567 A | 1/1999 | Ressemann |
| 5,868,702 A | 2/1999 | Stevens et al. |
| 5,876,414 A | 3/1999 | Straub |
| 5,885,238 A * | 3/1999 | Stevens ................ A61B 17/29 128/898 |
| 5,885,244 A | 3/1999 | Leone et al. |
| 5,893,857 A | 4/1999 | Shturman et al. |
| 5,895,398 A | 4/1999 | Wensel et al. |
| 5,895,399 A | 4/1999 | Barbut et al. |
| 5,908,395 A * | 6/1999 | Stalker ............ A61M 25/09041 600/585 |
| 5,910,252 A | 6/1999 | Truitt et al. |
| 5,911,722 A | 6/1999 | Adler et al. |
| 5,916,192 A | 6/1999 | Nita et al. |
| 5,921,958 A | 7/1999 | Ressemann et al. |
| 5,938,645 A | 8/1999 | Gordon |
| 5,941,871 A | 8/1999 | Adams et al. |
| 5,957,901 A | 9/1999 | Mottola et al. |
| 5,989,210 A | 11/1999 | Morris et al. |
| 6,007,513 A * | 12/1999 | Anis ................ A61F 9/00745 604/22 |
| 6,019,728 A | 2/2000 | Iwata et al. |
| 6,022,336 A | 2/2000 | Zadno-Azizi et al. |
| 6,027,460 A | 2/2000 | Shturman |
| 6,080,170 A | 6/2000 | Nash et al. |
| 6,096,001 A | 8/2000 | Drasler et al. |
| 6,126,635 A | 10/2000 | Simpson et al. |
| 6,129,697 A | 10/2000 | Drasler et al. |
| 6,129,698 A | 10/2000 | Beck |
| 6,146,396 A | 11/2000 | Kónya et al. |
| 6,156,046 A | 12/2000 | Passafaro et al. |
| 6,159,230 A | 12/2000 | Samuels |
| 6,165,188 A | 12/2000 | Saadat et al. |
| 6,176,844 B1 | 1/2001 | Lee |
| 6,179,809 B1 | 1/2001 | Khairkhahan et al. |
| 6,179,851 B1 | 1/2001 | Barbut et al. |

(56) References Cited

U.S. PATENT DOCUMENTS

| | | |
|---|---|---|
| 6,183,432 B1 | 2/2001 | Milo |
| 6,190,357 B1 | 2/2001 | Ferrari et al. |
| 6,196,989 B1 | 3/2001 | Padget et al. |
| 6,206,898 B1 | 3/2001 | Honeycutt et al. |
| 6,224,570 B1 | 5/2001 | Le et al. |
| 6,238,405 B1 | 5/2001 | Findlay, III et al. |
| 6,258,061 B1 | 7/2001 | Drasler et al. |
| 6,283,719 B1 | 9/2001 | Frantz et al. |
| 6,293,960 B1 | 9/2001 | Ken |
| 6,348,040 B1 | 2/2002 | Stalker et al. |
| 6,375,635 B1 | 4/2002 | Moutafis et al. |
| 6,440,148 B1* | 8/2002 | Shiber ............ A61B 8/12 606/159 |
| 6,454,775 B1* | 9/2002 | Demarais ...... A61B 17/320725 606/128 |
| 6,471,683 B2 | 10/2002 | Drasler et al. |
| 6,481,439 B1 | 11/2002 | Lewis et al. |
| 6,488,672 B1 | 12/2002 | Dance et al. |
| 6,533,772 B1 | 3/2003 | Sherts et al. |
| 6,544,209 B1 | 4/2003 | Drasler et al. |
| 6,544,231 B1 | 4/2003 | Palmer et al. |
| 6,551,302 B1 | 4/2003 | Rosinko et al. |
| 6,554,794 B1 | 4/2003 | Mueller et al. |
| 6,554,799 B1 | 4/2003 | Hatamura et al. |
| 6,558,401 B1 | 5/2003 | Azizi |
| 6,569,147 B1 | 5/2003 | Evans et al. |
| 6,569,148 B2 | 5/2003 | Bagaoisan et al. |
| 6,572,578 B1 | 6/2003 | Blanchard |
| 6,579,270 B2 | 6/2003 | Sussman et al. |
| 6,585,705 B1 | 7/2003 | Maginot et al. |
| 6,599,271 B1 | 7/2003 | Easley |
| 6,616,679 B1 | 9/2003 | Khosravi et al. |
| 6,622,367 B1 | 9/2003 | Bolduc et al. |
| 6,623,495 B2 | 9/2003 | Findlay, III et al. |
| 6,635,070 B2* | 10/2003 | Leeflang ............ A61B 17/22 606/200 |
| 6,652,548 B2 | 11/2003 | Evans et al. |
| 6,663,613 B1 | 12/2003 | Evans et al. |
| 6,676,637 B1 | 1/2004 | Bonnette et al. |
| 6,702,830 B1 | 3/2004 | Demarais et al. |
| 6,719,717 B1 | 4/2004 | Johnson et al. |
| 6,723,081 B1 | 4/2004 | Hektner |
| 6,726,675 B1 | 4/2004 | Beyar |
| 6,752,800 B1 | 6/2004 | Winston et al. |
| 6,755,803 B1 | 6/2004 | Le et al. |
| 6,755,812 B2 | 6/2004 | Peterson et al. |
| 6,790,215 B2 | 9/2004 | Findlay, III et al. |
| 6,818,001 B2 | 11/2004 | Wulfman et al. |
| 6,824,545 B2 | 11/2004 | Sepetka et al. |
| 6,824,550 B1 | 11/2004 | Noriega et al. |
| 6,830,577 B2 | 12/2004 | Nash et al. |
| 6,926,726 B2 | 8/2005 | Drasler et al. |
| 6,929,633 B2 | 8/2005 | Evans et al. |
| 6,936,056 B2 | 8/2005 | Nash et al. |
| 6,945,977 B2 | 9/2005 | Demarais et al. |
| 6,958,059 B2 | 10/2005 | Zadno-Azizi |
| 6,986,778 B2 | 1/2006 | Zadno-Azizi |
| 6,991,625 B1 | 1/2006 | Gately et al. |
| 7,008,434 B2 | 3/2006 | Kurz et al. |
| 7,044,958 B2 | 5/2006 | Douk et al. |
| 7,108,704 B2 | 9/2006 | Trerotola |
| 7,232,452 B2 | 6/2007 | Adams et al. |
| 7,374,560 B2 | 5/2008 | Ressemann et al. |
| 7,481,222 B2 | 1/2009 | Reissmann |
| 7,588,033 B2 | 9/2009 | Wondka |
| 7,591,816 B2 | 9/2009 | Wang et al. |
| 7,604,612 B2 | 10/2009 | Ressemann et al. |
| 7,615,042 B2 | 11/2009 | Beyer et al. |
| 7,621,886 B2 | 11/2009 | Burnett |
| 7,655,016 B2 | 2/2010 | Demarais et al. |
| 7,666,161 B2 | 2/2010 | Nash et al. |
| 7,699,804 B2 | 4/2010 | Barry et al. |
| 7,713,235 B2 | 5/2010 | Torrance et al. |
| 7,717,898 B2 | 5/2010 | Gately et al. |
| 7,736,355 B2* | 6/2010 | Itou ............ A61B 17/22 604/264 |
| 7,753,868 B2 | 7/2010 | Hoffa |
| 7,753,880 B2 | 7/2010 | Malackowski |
| 7,766,894 B2 | 8/2010 | Weitzner et al. |
| 7,776,005 B2 | 8/2010 | Haggstrom et al. |
| 7,798,996 B1 | 9/2010 | Haddad et al. |
| 7,798,999 B2 | 9/2010 | Bailey et al. |
| 7,806,864 B2 | 10/2010 | Haddad et al. |
| 7,833,239 B2 | 11/2010 | Nash |
| 7,846,175 B2 | 12/2010 | Bonnette et al. |
| 7,862,575 B2 | 1/2011 | Tal |
| 7,867,192 B2 | 1/2011 | Bowman et al. |
| 7,875,004 B2 | 1/2011 | Yodfat et al. |
| 7,879,022 B2* | 2/2011 | Bonnette ............ A61B 17/22 604/43 |
| 7,887,510 B2 | 2/2011 | Karpowicz et al. |
| 7,905,710 B2 | 3/2011 | Wang et al. |
| 7,909,801 B2 | 3/2011 | Hinchliffe |
| 7,909,810 B2 | 3/2011 | Noone |
| 7,914,482 B2 | 3/2011 | Urich et al. |
| 7,914,549 B2 | 3/2011 | Morsi |
| 7,918,654 B2 | 4/2011 | Adahan |
| 7,918,822 B2 | 4/2011 | Kumar et al. |
| 7,918,835 B2 | 4/2011 | Callahan et al. |
| 7,935,077 B2 | 5/2011 | Thor et al. |
| 7,951,073 B2 | 5/2011 | Freed |
| 7,951,112 B2 | 5/2011 | Petzer |
| 7,959,603 B2 | 6/2011 | Wahr et al. |
| 7,959,608 B2 | 6/2011 | Nash et al. |
| 7,976,528 B2 | 7/2011 | Nash et al. |
| 7,981,128 B2 | 7/2011 | To et al. |
| 7,981,129 B2 | 7/2011 | Nash et al. |
| 7,998,114 B2 | 8/2011 | Lombardi |
| 8,007,490 B2 | 8/2011 | Schaeffer et al. |
| 8,012,766 B2 | 9/2011 | Graham |
| 8,021,351 B2 | 9/2011 | Boldenow et al. |
| 8,034,018 B2 | 10/2011 | Lutwyche |
| 8,043,312 B2 | 10/2011 | Noriega et al. |
| 8,043,313 B2 | 10/2011 | Krolik et al. |
| 8,062,246 B2 | 11/2011 | Moutafis et al. |
| 8,062,257 B2 | 11/2011 | Moberg et al. |
| 8,065,096 B2 | 11/2011 | Moberg et al. |
| 8,066,677 B2 | 11/2011 | Lunn et al. |
| 8,070,694 B2 | 12/2011 | Galdonik et al. |
| 8,075,546 B2 | 12/2011 | Carlisle et al. |
| 8,092,483 B2 | 1/2012 | Galdonik et al. |
| 8,140,146 B2 | 3/2012 | Kim et al. |
| 8,142,458 B2 | 3/2012 | Shturman |
| 8,152,782 B2 | 4/2012 | Jang et al. |
| 8,152,951 B2 | 4/2012 | Zawacki et al. |
| 8,157,787 B2 | 4/2012 | Nash et al. |
| 8,162,877 B2 | 4/2012 | Bonnette et al. |
| 8,177,739 B2 | 5/2012 | Cartledge et al. |
| 8,182,462 B2 | 5/2012 | Istoc et al. |
| 8,187,228 B2 | 5/2012 | Bikovsky |
| 8,187,229 B2 | 5/2012 | Weitzner et al. |
| 8,202,243 B2 | 6/2012 | Morgan |
| 8,209,060 B2 | 6/2012 | Ledford |
| 8,221,348 B2 | 7/2012 | Hackett et al. |
| 8,226,673 B2 | 7/2012 | Nash et al. |
| 8,246,573 B2 | 8/2012 | Ali et al. |
| 8,246,580 B2 | 8/2012 | Hopkins et al. |
| 8,257,298 B2 | 9/2012 | Hamboly |
| 8,257,343 B2 | 9/2012 | Chan et al. |
| 8,262,645 B2 | 9/2012 | Bagwell et al. |
| 8,267,893 B2 | 9/2012 | Moberg et al. |
| 8,287,485 B2 | 10/2012 | Kimura et al. |
| 8,291,337 B2 | 10/2012 | Gannin et al. |
| 8,292,841 B2 | 10/2012 | Gregersen |
| 8,317,739 B2 | 11/2012 | Kuebler |
| 8,317,770 B2 | 11/2012 | Miesel et al. |
| 8,317,773 B2 | 11/2012 | Appling et al. |
| 8,317,786 B2 | 11/2012 | Dahla et al. |
| 8,323,239 B2 | 12/2012 | Bednarek et al. |
| 8,323,268 B2 | 12/2012 | Ring et al. |
| 8,337,175 B2 | 12/2012 | Dion et al. |
| 8,343,097 B2 | 1/2013 | Pile-Spellman et al. |
| 8,343,131 B2 | 1/2013 | Vinten-Johansen |

(56) References Cited

U.S. PATENT DOCUMENTS

| | | |
|---|---|---|
| 8,348,896 B2 | 1/2013 | Wagner |
| 8,353,858 B2 | 1/2013 | Kozak et al. |
| 8,353,860 B2 | 1/2013 | Boulais et al. |
| 8,357,138 B2 | 1/2013 | Pierpont et al. |
| 8,372,038 B2 | 2/2013 | Urich et al. |
| 8,394,078 B2 | 3/2013 | Torrance et al. |
| 8,398,581 B2 | 3/2013 | Panotopoulos |
| 8,398,582 B2 | 3/2013 | Gordon et al. |
| 8,414,521 B2 | 4/2013 | Baker et al. |
| 8,414,522 B2 | 4/2013 | Kamen et al. |
| 8,414,943 B2 | 4/2013 | McGuckin, Jr. et al. |
| 8,419,709 B2 | 4/2013 | Haddad et al. |
| 8,425,458 B2 | 4/2013 | Scopton |
| 8,430,837 B2 | 4/2013 | Jenson et al. |
| 8,430,845 B2 | 4/2013 | Wahr et al. |
| 8,430,861 B2 | 4/2013 | Schwartz et al. |
| 8,439,876 B2 | 5/2013 | Spohn et al. |
| 8,454,557 B1 | 6/2013 | Qi et al. |
| 8,465,456 B2 | 6/2013 | Stivland |
| 8,465,867 B2 | 6/2013 | Kim |
| 8,483,980 B2 | 7/2013 | Moberg et al. |
| 8,491,523 B2 | 7/2013 | Thor et al. |
| 8,500,697 B2 | 8/2013 | Kurth et al. |
| 8,506,537 B2 | 8/2013 | Torstensen et al. |
| 8,523,801 B2 | 9/2013 | Nash et al. |
| 8,545,514 B2 | 10/2013 | Ferrera |
| 8,562,555 B2 | 10/2013 | MacMahon et al. |
| 8,597,238 B2 | 12/2013 | Bonnette et al. |
| 8,608,699 B2 | 12/2013 | Blomquist |
| 8,613,618 B2 | 12/2013 | Brokx |
| 8,613,724 B2 | 12/2013 | Lanier, Jr. et al. |
| 8,617,110 B2 | 12/2013 | Moberg et al. |
| 8,617,127 B2 | 12/2013 | Woolston et al. |
| 8,623,039 B2 | 1/2014 | Seto et al. |
| 8,628,549 B2 | 1/2014 | To et al. |
| 8,641,671 B2 | 2/2014 | Michaud et al. |
| 8,647,294 B2 | 2/2014 | Bonnette et al. |
| 8,652,086 B2 | 2/2014 | Gerg et al. |
| 8,657,777 B2 | 2/2014 | Kozak et al. |
| 8,657,785 B2 | 2/2014 | Torrance et al. |
| 8,663,259 B2 * | 3/2014 | Levine ............ A61B 17/320758 606/159 |
| 8,668,464 B2 | 3/2014 | Kensy et al. |
| 8,668,665 B2 | 3/2014 | Gerg et al. |
| 8,670,836 B2 | 3/2014 | Aeschlimann et al. |
| 8,672,876 B2 | 3/2014 | Jacobson et al. |
| 8,681,010 B2 | 3/2014 | Moberg et al. |
| 8,721,674 B2 | 5/2014 | Kusleika |
| 8,758,325 B2 | 6/2014 | Webster et al. |
| 8,758,364 B2 | 6/2014 | Eckhouse et al. |
| 8,783,151 B1 | 6/2014 | Janardhan et al. |
| 8,803,030 B1 | 8/2014 | Janardhan et al. |
| 8,814,892 B2 | 8/2014 | Galdonik et al. |
| 8,852,219 B2 | 10/2014 | Wulfman et al. |
| 8,864,792 B2 | 10/2014 | Eckhouse et al. |
| 8,888,801 B2 | 11/2014 | To et al. |
| 8,920,402 B2 | 12/2014 | Nash et al. |
| 8,970,384 B2 | 3/2015 | Yodfat et al. |
| 8,986,241 B2 | 3/2015 | Evans et al. |
| 9,005,237 B2 | 4/2015 | Eckhouse et al. |
| 9,017,294 B2 | 4/2015 | McGuckin et al. |
| 9,023,070 B2 | 5/2015 | Levine et al. |
| 9,034,008 B2 | 5/2015 | Eckhouse et al. |
| 9,113,955 B2 | 8/2015 | Noriega et al. |
| 9,119,941 B2 | 9/2015 | Rollins et al. |
| 9,119,942 B1 | 9/2015 | Rollins et al. |
| 9,198,679 B2 | 12/2015 | To et al. |
| 9,248,221 B2 | 2/2016 | Look et al. |
| 9,282,992 B2 | 3/2016 | Levine et al. |
| 9,283,040 B2 | 3/2016 | Hendrick et al. |
| 9,308,016 B2 | 4/2016 | Escudero et al. |
| 9,314,263 B2 | 4/2016 | Escudero et al. |
| 9,332,999 B2 | 5/2016 | Ray et al. |
| 9,333,007 B2 | 5/2016 | Escudero et al. |
| 9,433,427 B2 | 9/2016 | Look et al. |
| 9,456,872 B2 | 10/2016 | Hendrick et al. |
| 9,474,543 B2 | 10/2016 | McGuckin et al. |
| 9,492,192 B2 | 11/2016 | To et al. |
| 9,492,193 B2 | 11/2016 | To et al. |
| 9,700,346 B2 | 7/2017 | Levine et al. |
| 9,795,406 B2 | 10/2017 | Levine et al. |
| 2001/0004700 A1 | 6/2001 | Honeycutt et al. |
| 2001/0051811 A1 | 12/2001 | Bonnette et al. |
| 2002/0029052 A1 * | 3/2002 | Evans ................ A61B 17/22 606/159 |
| 2002/0068895 A1 | 6/2002 | Beck |
| 2002/0133114 A1 | 9/2002 | Itoh et al. |
| 2002/0138095 A1 | 9/2002 | Mazzocchi et al. |
| 2002/0165575 A1 | 11/2002 | Saleh |
| 2002/0173819 A1 | 11/2002 | Leeflang et al. |
| 2002/0177789 A1 | 11/2002 | Ferry et al. |
| 2003/0032918 A1 | 2/2003 | Quinn |
| 2003/0040694 A1 | 2/2003 | Dorros et al. |
| 2003/0069549 A1 | 4/2003 | MacMahon et al. |
| 2003/0088187 A1 | 5/2003 | Saadat et al. |
| 2003/0088209 A1 | 5/2003 | Chiu et al. |
| 2003/0139751 A1 * | 7/2003 | Evans ................ A61B 17/22 606/127 |
| 2003/0144688 A1 | 7/2003 | Brady et al. |
| 2003/0216760 A1 * | 11/2003 | Welch ................ A61B 17/22 606/159 |
| 2003/0220556 A1 | 11/2003 | Porat et al. |
| 2003/0236533 A1 | 12/2003 | Wilson et al. |
| 2004/0049225 A1 | 3/2004 | Denison |
| 2004/0054322 A1 | 3/2004 | Vargas |
| 2004/0087988 A1 * | 5/2004 | Heitzmann ..... A61B 17/320758 606/159 |
| 2004/0147871 A1 | 7/2004 | Burnett |
| 2004/0158136 A1 | 8/2004 | Gough et al. |
| 2004/0167463 A1 | 8/2004 | Zawacki |
| 2004/0193046 A1 | 9/2004 | Nash et al. |
| 2004/0199201 A1 | 10/2004 | Kellet et al. |
| 2004/0215222 A1 * | 10/2004 | krivoruchko .. A61B 17/320725 606/159 |
| 2004/0236214 A1 | 11/2004 | Opie et al. |
| 2004/0243157 A1 | 12/2004 | Connor et al. |
| 2005/0065426 A1 | 3/2005 | Porat et al. |
| 2005/0102165 A1 | 5/2005 | Oshita et al. |
| 2005/0159716 A1 | 7/2005 | Kobayashi et al. |
| 2005/0196748 A1 | 9/2005 | Ericson |
| 2005/0238503 A1 | 10/2005 | Rush et al. |
| 2005/0240116 A1 | 10/2005 | Saadat et al. |
| 2005/0240120 A1 | 10/2005 | Modesitt |
| 2005/0240146 A1 | 10/2005 | Nash et al. |
| 2005/0244521 A1 | 11/2005 | Strickland et al. |
| 2005/0277851 A1 | 12/2005 | Whittaker et al. |
| 2006/0009785 A1 | 1/2006 | Maitland et al. |
| 2006/0041245 A1 | 2/2006 | Ferry et al. |
| 2006/0058836 A1 | 3/2006 | Bose et al. |
| 2006/0064123 A1 | 3/2006 | Bonnette et al. |
| 2006/0074442 A1 | 4/2006 | Noriega et al. |
| 2006/0093989 A1 | 5/2006 | Hahn et al. |
| 2006/0142630 A1 | 6/2006 | Meretei |
| 2006/0184186 A1 | 8/2006 | Noone |
| 2006/0229550 A1 | 10/2006 | Staid et al. |
| 2006/0229587 A1 | 10/2006 | Beyar et al. |
| 2006/0282150 A1 | 12/2006 | Olson et al. |
| 2007/0016105 A1 | 1/2007 | Mamourian |
| 2007/0060879 A1 | 3/2007 | Weitzner et al. |
| 2007/0073233 A1 | 3/2007 | Thor et al. |
| 2007/0073268 A1 | 3/2007 | Goble et al. |
| 2007/0078438 A1 | 4/2007 | Okada |
| 2007/0118165 A1 | 5/2007 | DeMello et al. |
| 2007/0167804 A1 | 7/2007 | Park et al. |
| 2007/0197956 A1 | 8/2007 | Le et al. |
| 2007/0219467 A1 * | 9/2007 | Clark ................. A61M 25/0113 600/585 |
| 2007/0225615 A1 | 9/2007 | Chechelski et al. |
| 2007/0225739 A1 | 9/2007 | Pintor et al. |
| 2007/0239182 A1 * | 10/2007 | Glines ............ A61B 17/22012 606/159 |
| 2007/0270755 A1 | 11/2007 | Von Oepen et al. |
| 2007/0299306 A1 | 12/2007 | Parasher et al. |
| 2008/0009784 A1 | 1/2008 | Leedle et al. |

(56) References Cited

U.S. PATENT DOCUMENTS

| | | |
|---|---|---|
| 2008/0097339 A1 | 4/2008 | Ranchod et al. |
| 2008/0097465 A1* | 4/2008 | Rollins ............ A61M 25/09041 606/108 |
| 2008/0097563 A1 | 4/2008 | Petrie et al. |
| 2008/0119824 A1 | 5/2008 | Weitzner et al. |
| 2008/0125798 A1* | 5/2008 | Osborne .............. A61B 17/221 606/159 |
| 2008/0195139 A1 | 8/2008 | Donald et al. |
| 2008/0249501 A1 | 10/2008 | Yamasaki |
| 2008/0255539 A1 | 10/2008 | Booth |
| 2008/0255596 A1 | 10/2008 | Jenson et al. |
| 2008/0294181 A1 | 11/2008 | Wensel et al. |
| 2008/0306465 A1 | 12/2008 | Bailey et al. |
| 2008/0319376 A1 | 12/2008 | Wilcox et al. |
| 2009/0018566 A1* | 1/2009 | Escudero ....... A61B 17/320758 606/159 |
| 2009/0054825 A1 | 2/2009 | Melsheimer et al. |
| 2009/0082722 A1 | 3/2009 | Munger et al. |
| 2009/0105645 A1 | 4/2009 | Kidd et al. |
| 2009/0105690 A1 | 4/2009 | Schaeffer et al. |
| 2009/0157057 A1 | 6/2009 | Ferren et al. |
| 2009/0264940 A1* | 10/2009 | Beale ................. A61B 5/04001 606/86 R |
| 2009/0292212 A1 | 11/2009 | Ferren et al. |
| 2010/0030186 A1 | 2/2010 | Stivland |
| 2010/0094201 A1 | 4/2010 | Mallaby |
| 2010/0174233 A1 | 7/2010 | Kuban et al. |
| 2010/0204613 A1* | 8/2010 | Rollins ............ A61M 25/09041 600/585 |
| 2010/0204672 A1* | 8/2010 | Lockhart ................ A61B 17/22 604/500 |
| 2010/0217275 A1 | 8/2010 | Carmeli et al. |
| 2010/0217276 A1 | 8/2010 | Garrison et al. |
| 2010/0274191 A1 | 10/2010 | Ting |
| 2010/0280534 A1* | 11/2010 | Sher ............... A61B 17/320758 606/159 |
| 2011/0106019 A1 | 5/2011 | Bagwell et al. |
| 2011/0152920 A1 | 6/2011 | Eckhouse et al. |
| 2011/0160683 A1 | 6/2011 | Pinotti Barbosa et al. |
| 2012/0059340 A1 | 3/2012 | Larsson |
| 2012/0065660 A1 | 3/2012 | Ferrera et al. |
| 2012/0071907 A1* | 3/2012 | Pintor ............ A61B 17/320758 606/159 |
| 2012/0078080 A1 | 3/2012 | Foley et al. |
| 2012/0123509 A1 | 5/2012 | Merrill et al. |
| 2012/0130415 A1 | 5/2012 | Tal et al. |
| 2012/0165756 A1 | 6/2012 | Root et al. |
| 2012/0239064 A1* | 9/2012 | Cartier ................ A61B 17/221 606/159 |
| 2012/0239066 A1* | 9/2012 | Levine ............ A61B 17/320758 606/159 |
| 2012/0259265 A1 | 10/2012 | Salehi et al. |
| 2012/0289910 A1 | 11/2012 | Shtul et al. |
| 2012/0291811 A1 | 11/2012 | Dabney et al. |
| 2013/0190701 A1 | 7/2013 | Kim |
| 2013/0218186 A1* | 8/2013 | Dubois ............ A61B 17/32002 606/180 |
| 2013/0267891 A1 | 10/2013 | Malhi et al. |
| 2013/0281788 A1* | 10/2013 | Garrison ............ A61B 17/3415 600/208 |
| 2013/0310845 A1 | 11/2013 | Thor et al. |
| 2014/0005699 A1 | 1/2014 | Bonnette et al. |
| 2014/0142594 A1* | 5/2014 | Fojtik .................. A61M 25/09 606/130 |
| 2014/0147246 A1 | 5/2014 | Chappel et al. |
| 2014/0148830 A1* | 5/2014 | Bowman ........ A61B 17/320758 606/159 |
| 2014/0155931 A1 | 6/2014 | Bose et al. |
| 2014/0228869 A1 | 8/2014 | Bonnette et al. |
| 2014/0276920 A1 | 9/2014 | Hendrick et al. |
| 2014/0309589 A1 | 10/2014 | Momose et al. |
| 2014/0323906 A1 | 10/2014 | Peatfield et al. |
| 2015/0094748 A1 | 4/2015 | Nash et al. |
| 2015/0327875 A1 | 11/2015 | Look et al. |

FOREIGN PATENT DOCUMENTS

| | | |
|---|---|---|
| EP | 806213 A1 | 11/1997 |
| EP | 726466 B1 | 4/2002 |
| EP | 1488748 A1 | 12/2004 |
| EP | 2301450 B1 | 11/2011 |
| JP | 2003260127 A | 9/2003 |
| WO | WO199005493 A1 | 5/1990 |
| WO | WO1996001079 A1 | 1/1996 |
| WO | WO1996035469 A1 | 11/1996 |
| WO | WO199918850 A1 | 4/1999 |
| WO | WO2001037916 A1 | 5/2001 |
| WO | WO2004100772 A2 | 11/2004 |
| WO | WO2007143633 A2 | 12/2007 |
| WO | WO2008097993 A2 | 8/2008 |
| WO | WO 2010/023617 A2 | 3/2010 |
| WO | WO2017/112922 A1 | 6/2017 |

OTHER PUBLICATIONS

Frölich, G., Meier, P., White, S., Yellon, D., Hausenloy, D., "Myocardial reperfusion injury: looking beyond primary PCI", European Heart Journal Jun. 2013, pp. 1714-1722, vol. 34, No. 23, Elsevier, Amsterdam, The Netherlands.

Gousios, A., Shearn, M, "Effect of Intravenous Heparin on Human Blood Viscosity", Circulation, Dec. 1959, pp. 1063-1066, vol. 20, American Heart Association, Dallas, USA.

"Infusion Liquid Flow Sensors—Safe, Precise and Reliable", Sensirion, downloaded from internet Apr. 3, 2015.

"Makes even the most difficult intervention a Fast and Smooth Run." GuideLiner brochure. Vascular Solutions, Inc., downloaded from internet Apr. 9, 2015.

Parikh, A., Ali, F., "Novel Use of GuideLiner Catheter to Perform Aspiration Thrombectomy in a Saphenous Vein Graft" Cath Lab Digest, Oct. 2013, downloaded from internet Oct. 22, 2014.

Prasad, A., Stone, G., Holmes, D., Gersh, B., Peperfusion Injury, Microvascular Dysfunction, and Carioprotection: The "Dark Side" of Reperfusion, Circulation, Nov. 24, 2009, pp. 2105-2112, vol. 120, American Heart Association, Dallas, USA.

Rodriquez, R., Condé-Green, A., "Quantification of Negative Pressures Generated by Syringes of Different Calibers Used for Liposuction", Plastic & Reconstructive Surgery, Aug. 2012, pp. 383e-384e, vol. 130, No. 2, Lippicott Williams & Wilkins, Philadelphia, USA.

Stys, A., Stys, T., Rajpurohit, N., Khan, M. "A Novel Application of GuideLiner Catheter for Thrombectomy in Acute Myocardial Infarction: A Case Series", Journal of Invasive cardiology, Nov. 2013, pp. 620-624, vol. 25, No. 11, King of Prussia, USA.

PCT International Search Report and Written Opinion for PCT/US2016/050302, Applicant: Vesatek, LLC, Forms PCT/ISA/220, 210, and 237 dated Nov. 29, 2016 (10 pages).

Extended European Search Report dated Aug. 31,2018, in EP App. No. 16843162.5 filed Sep. 3, 2016 (10 pages).

JP2003260127A (Machine Translation, Sep. 7, 2018) (5 pages).

* cited by examiner

SYSTEMS AND METHODS FOR MANIPULATING MEDICAL DEVICES

INCORPORATION BY REFERENCE TO ANY PRIORITY APPLICATIONS

This application claims the benefit of priority to U.S. Provisional Application No. 62/214,192, filed on Sep. 3, 2015, and U.S. Provisional Application No. 62/286,429, filed on Jan. 24, 2016, both of which are herein incorporated by reference in their entirety for all purposes. Priority is claimed pursuant to 35 U.S.C. § 119.

BACKGROUND OF THE INVENTION

Guidewires and other elongate medical devices are configured to be placed within conduits and cavities of the body. These devices may be manipulated manually to move or track the devices through tortuous, obstructed, or stenosed passageways. Such maneuvers are oftentimes challenging and require skill and experience. At times, it is impossible to successfully move or track the devices to desired target locations within the body.

SUMMARY OF THE INVENTION

In a first embodiment of the present disclosure, a method for treating a patient having thrombus includes providing a manipulation device including a housing configured to be supported by the hand of a user, the housing having a distal end and a proximal end, a drive system disposed within the housing, and configured to rotate a rotation member, an engagement member coupled to the rotation member, and configured to be removably coupled to an elongate medical device to transfer rotational movement of the rotation member to rotational movement of an elongate medical device, an activation member carried by the housing such that it can be operated by at least a portion of the hand of the user when the housing is supported by the hand of the user, and wherein the drive system if configured to apply motive force to the engagement member, securing an elongate member to the engagement member, the elongate member having a distal end configured for introduction into a patient's vasculature, introducing at least the distal end of the elongate member into a blood vessel adjacent a thrombus, operating the activation member to cause at least some rotation of the rotation member, which in turn causes at least some rotation of the distal end of the elongate member at or near the thrombus, and aspirating at least some of the thrombus with an aspiration catheter.

In another embodiment of the present disclosure, system for treating a patient having thrombus includes an aspiration catheter having a distal end, a proximal end, and an aspiration lumen extending between the distal end and the proximal end and configured to be coupled to a vacuum source, an elongate member having a distal end and a proximal end, and configured for placement through the aspiration lumen of the aspiration catheter, a manipulation device including a housing configured to be supported by the hand of a user, the housing having a distal end and a proximal end, a drive system disposed within the housing, and configured to rotate a rotation member, an engagement member coupled to the rotation member, and configured to be removably coupled to the elongate member to transfer rotational movement of the rotation member to rotational movement of the elongate member, an activation member carried by the housing such that it can be operated by at least a portion of the hand of the user when the housing is supported by the hand of the user, and wherein the drive system if configured to apply motive force to the engagement member to thereby move the elongate member.

DETAILED DESCRIPTION OF THE ILLUSTRATED EMBODIMENTS

Embodiments of the present disclosure comprise systems and methods for manipulating one or more medical devices. The medical devices may include elongated medical devices including, but not limited to: guidewires (guide wires), maceration devices, for example maceration devices having an expending element (such as a basket), cutting devices, atherectomy devices, and a variety of different catheter shafts, including solid catheter shafts and hollow catheter shafts. Conventional guidewire manual manipulation methods often involve applying torque to the guidewire to aid its passage through tortuous, occluded, or stenosed conduits or vessels. The user may sometimes spin the guidewire within the fingers (e.g., gloved fingers) to create a torque which assists in manipulating the guidewire through the challenging anatomy. This technique is sometimes referred to as "helicoptering," alluding to the spinning blades of a helicopter. This technique can be difficult to achieve because the typically small diameter of guidewires makes them difficult to grip. Additionally, it may be difficult to apply necessary friction to the surface of the guidewire to cause them to rotate, because guidewires are often covered with a lubricious coating. For similar reasons, it may be difficult to place a longitudinal force on the guidewires with manual manipulation, including a back-and-forth longitudinal force intended for placing an oscillatory motion on the guidewire.

Figure 1:
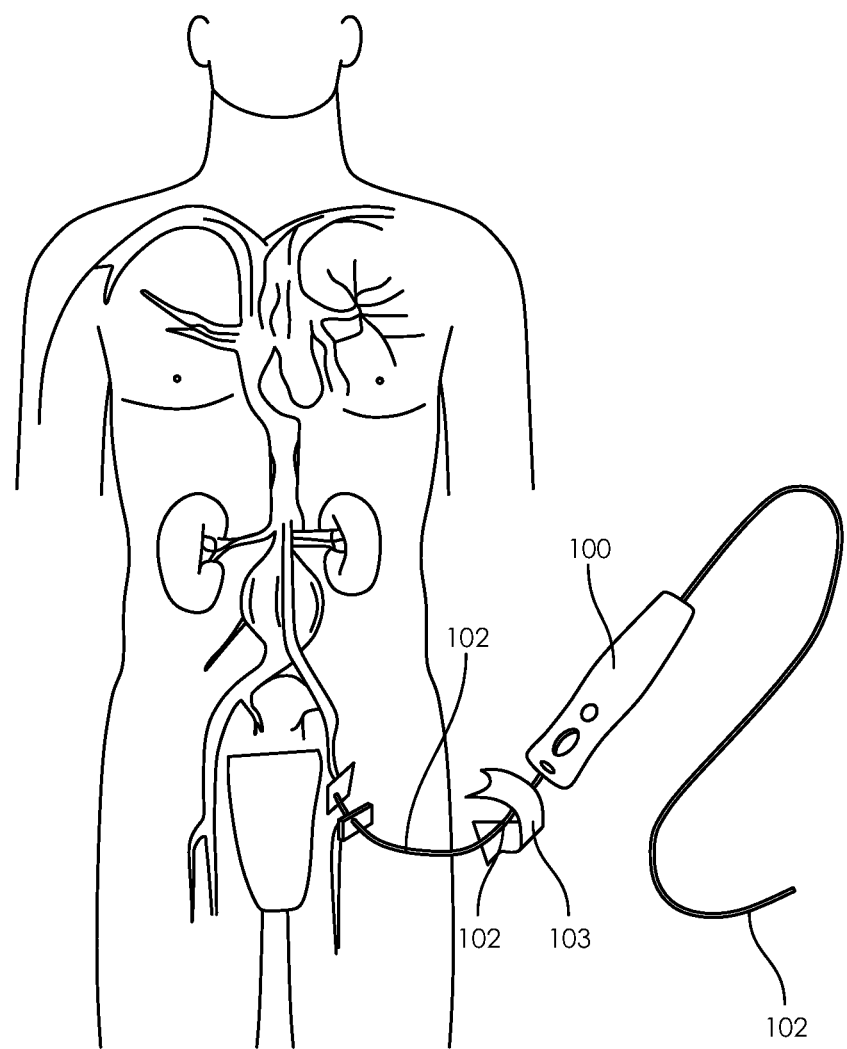
FIG. 1 illustrates a view of a guidewire manipulation device being used on a patient according to an embodiment of the present disclosure.

FIG. 1 illustrates an embodiment of a guidewire manipulation device 100 which is advanced over a guidewire 102. As seen in this figure, the guidewire 102 is introduced into a blood vessel of the patient (e.g., a femoral artery). The manipulation device 100 is slid over the guidewire 102 and selectively locked on to the guidewire 102. As the guidewire 102 is advance into the patient, the user operates the manipulation device 100 to rotate or vibrate the guidewire 102 as appropriate.

For example, as a distal end of the guidewire 102 reaches an angled or curved region of the vessel, the user activates the manipulation device 100 to rotate the guidewire 102 (i.e., in a counter clockwise direction indicated by arrow 103), thereby causing the distal end of the guidewire 102 to more easily advance through the angled or curved region. In another example, the distal end of the guidewire 102 reaches an obstruction (e.g., an embolism) but is unable to easily pass. The user then activates the guidewire manipulation device 100 to vibrate (e.g., by routing between a clockwise and counter clockwise direction quickly), thereby causing the distal end of the guidewire 102 to pass through the obstruction. In another example, the device 100 may include a multiple, preprogrammed rotation patterns appropriate for different vessel configurations (e.g., a 180 degree clockwise rotation followed by 180 degree counter-clockwise rotation, a 90 degree clockwise rotation followed by 90 degree counter clockwise rotation or a 30 degree clockwise rotation followed by 180 degree counter clockwise rotation).

Figure 2A:
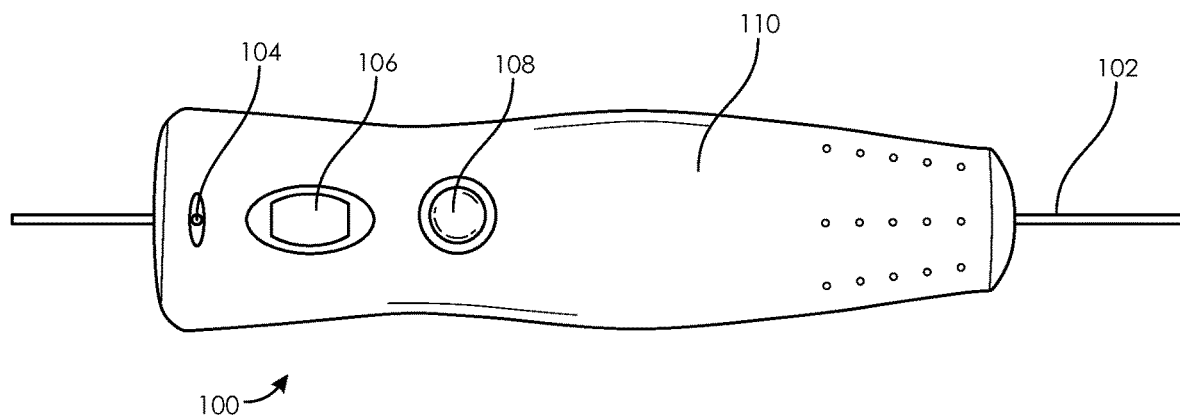
FIG. 2A illustrates a top view of the guidewire manipulation device of FIG. 1.
Figure 2B:
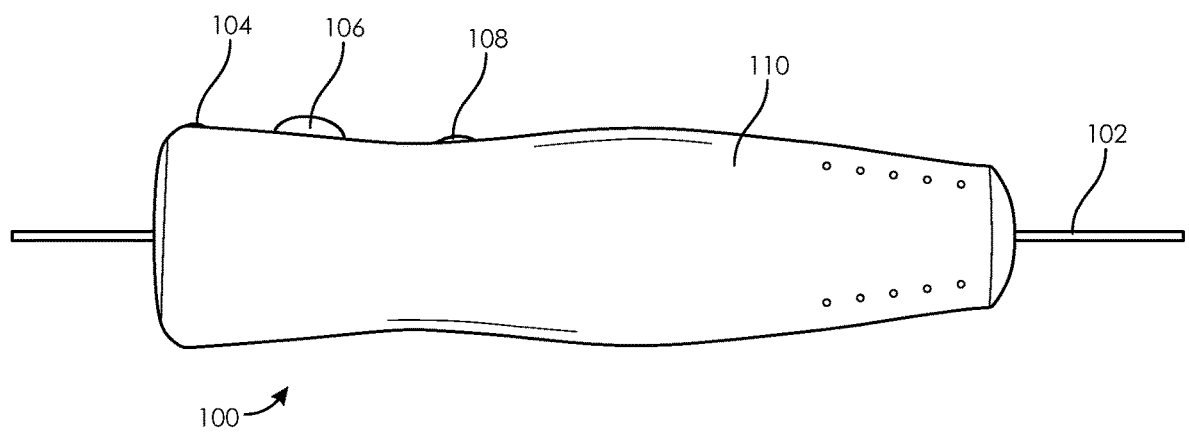
FIG. 2B illustrates a side view of the guidewire manipulation device of FIG. 1.

FIGS. 2A and 2B illustrate external views of the guidewire manipulation device 100. The guidewire manipulation device 100 may also include a microprocessor and memory connected to the motor and a button 108 for storing and executing the preprogrammed rotation patterns. As seen in these figures, the guidewire 102 passes through a passage along the length of the guidewire manipulation device 100. Preferably, the guidewire manipulation device 100 includes a locking assembly in the form of a guidewire lock switch 106 which allows the user to selectively lock the guidewire manipulation device 100 to the guidewire 102. In this respect, the guidewire manipulation device 100 can move relative to the guidewire 102 in an unlocked state, and can move the guidewire 102 (rotationally and/or longitudinally) in a locked state.

The guidewire manipulation device 100 also preferably includes a power indicator light 104 (e.g., an LED) which indicates if the device 100 is powered on and a rotation button 108 which causes the guidewire 102 to rotate. By pressing the button 108, the user activates the device 100. Optionally, the device 100 may include a button, switch or similar mechanism to toggle the device 100 between rotating in a clockwise direction or a counter-clockwise direction. Alternately, the button 108 may include multiple actuation techniques for determining clockwise or counter-clockwise rotation (e.g., sliding forward or backward, multiple button presses, etc.).

Preferably, an outer container or casing 110 is composed of a light-weight material such as plastic and has an ergonomic shape that at least partially fits in the user's hand. In this respect, the user can comfortably operate the guidewire manipulation device 100 during a procedure.

Figure 3:
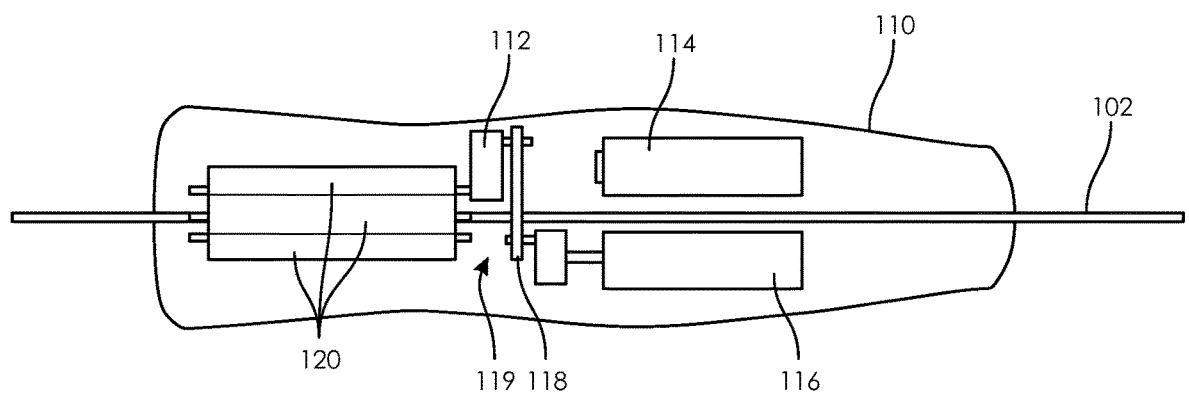
FIG. 3 frustrates a top open view of the guidewire manipulation device of FIG. 1.
Figure 4:
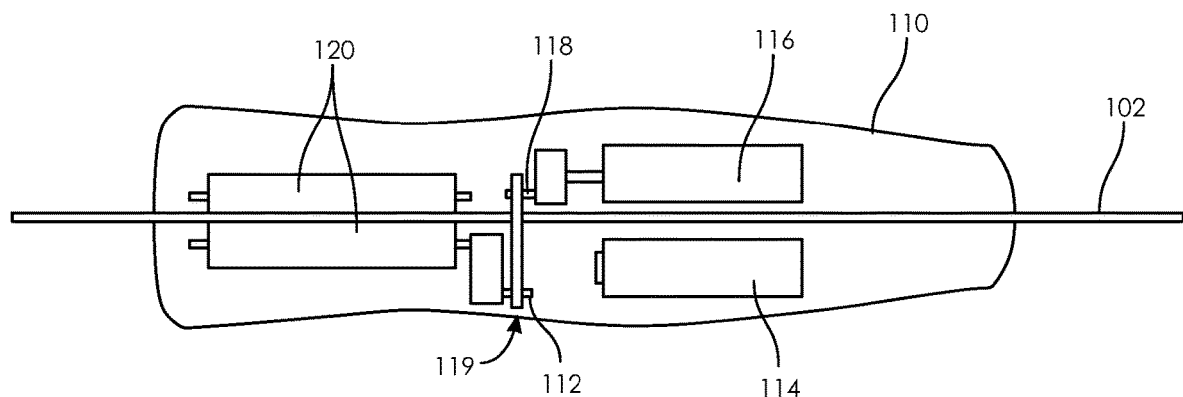
FIG. 4 illustrates a bottom open view of the guidewire manipulation device of FIG. 1.
Figure 5:
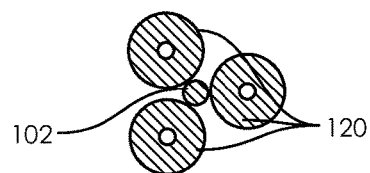
FIG. 5 illustrates a cross sectional view of the rollers of the guidewire manipulation device of FIG. 1.

Referring to FIGS. 3 and 4, an interior view of the guidewire manipulation device 100 within the outer casing 110 is illustrated according to an embodiment of the present disclosure. The guidewire 102 is engaged by the device 100 with elongated rollers 120 (also seen in the cross sectional view of FIG. 5). Preferably the device 100 includes at least three rollers, however, any number of rollers 120 are possible (e.g., 1-5 rollers). When; the button 108 is pressed, the rollers 120 rotate, thereby rotating the guidewire 102. Preferably, the lock switch 106 raises or lowers one or more of the rollers 120 in relation to the guidewire 102, so as to lock the guidewire 102 with the device 100 when the rollers 120 are pressed against the guidewire 102 and unlock the guidewire 102 from the device 100 when the roller(s) 120 are moved away from the guidewire 102.

One or more of the rollers 120 are preferably driven by a motor 116 which is powered by battery 114 (or alternately by A.C. power such as an outlet). The motor 116 connects to the roller(s) 120 by a cam 119 made up of a first linkage 118 connected to the motor 116 and a second linkage 112 connected to the roller(s) 120. In this respect, activation of the motor 116 drives the cam 119 and ultimately rotation of one or more of the rollers 120.

Figure 6:
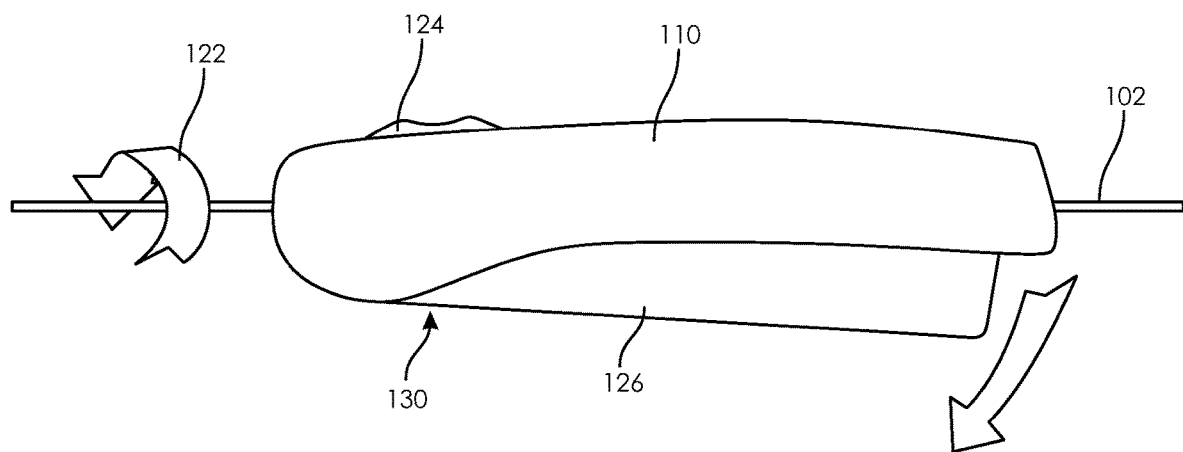
FIG. 6 illustrates a side view of a guidewire manipulation device according to an embodiment of the present disclosure.
Figure 7:
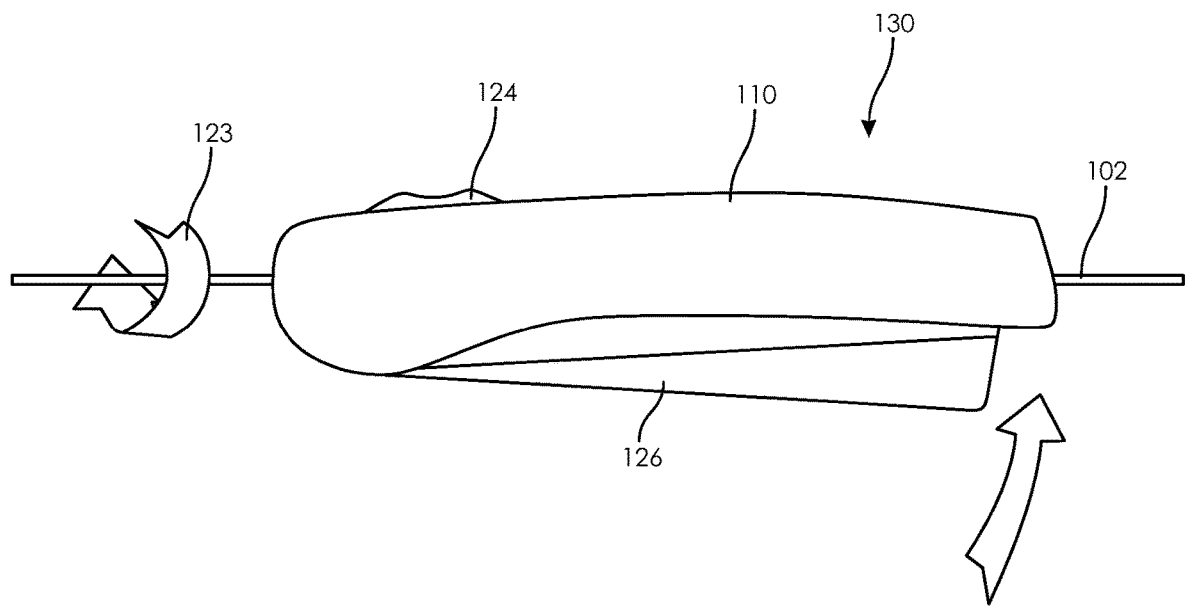
FIG. 7 illustrates a side view of the guidewire manipulation device of FIG. 6 with a depressed trigger according to an embodiment of the present disclosure.

FIGS. 6 and 7 illustrate another embodiment of a manual manipulation device 130 according to the present disclosure. The device 130 is generally similar to the previously described device 100, except that the rollers 120 and therefore rotation at the guidewire 102 is driven by a handle 126. For example, depressing the handle 126 rotates the guidewire 102 in a clockwise direction (arrow 122) and releasing the handle 126 rotates the guidewire 102 in a counter clockwise direction (arrow 123). Additionally, a switch 124 is included to change a type of rotation caused by the handle 126. For example, the switch 124 may change a gear ratio and therefore the amount of rotation cause by depressing the handle. In another example, the switch 124 may change directions of rotation caused by depressing the handle 126. By manual activation of the handle 126 by the user, the internal drive components drive the rotation of the guidewire 102 without the need of a motor 116.

Figure 8:
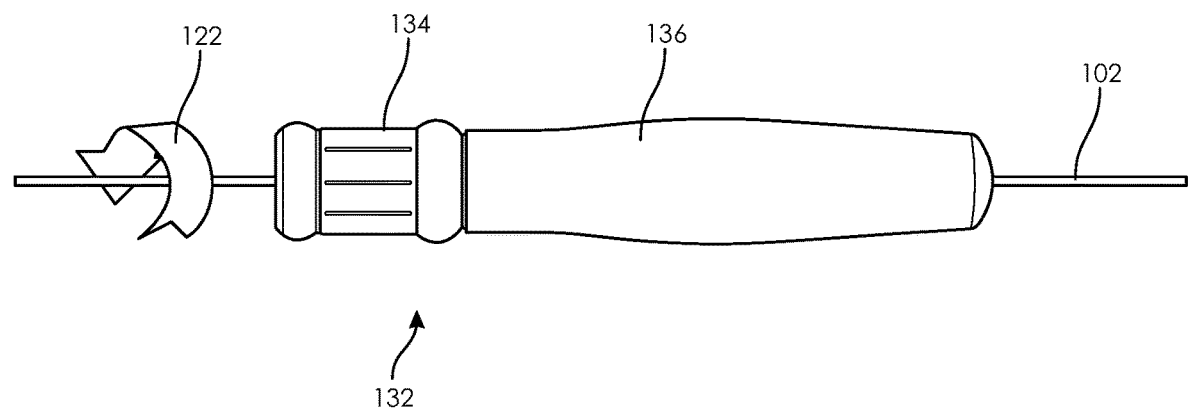
FIG. 8 illustrates a side view of a guidewire manipulation device according to an embodiment of the present disclosure.
Figure 9:
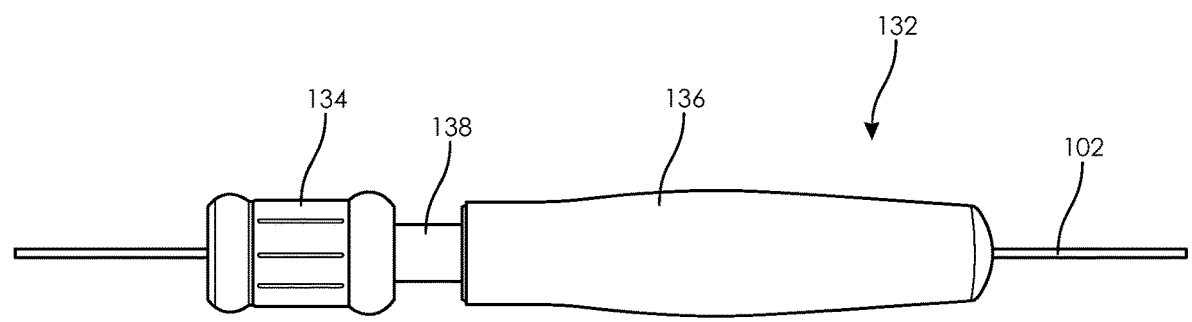
FIG. 9 illustrates a side view of the guide-wire manipulation device of FIG. 8.
Figure 10:
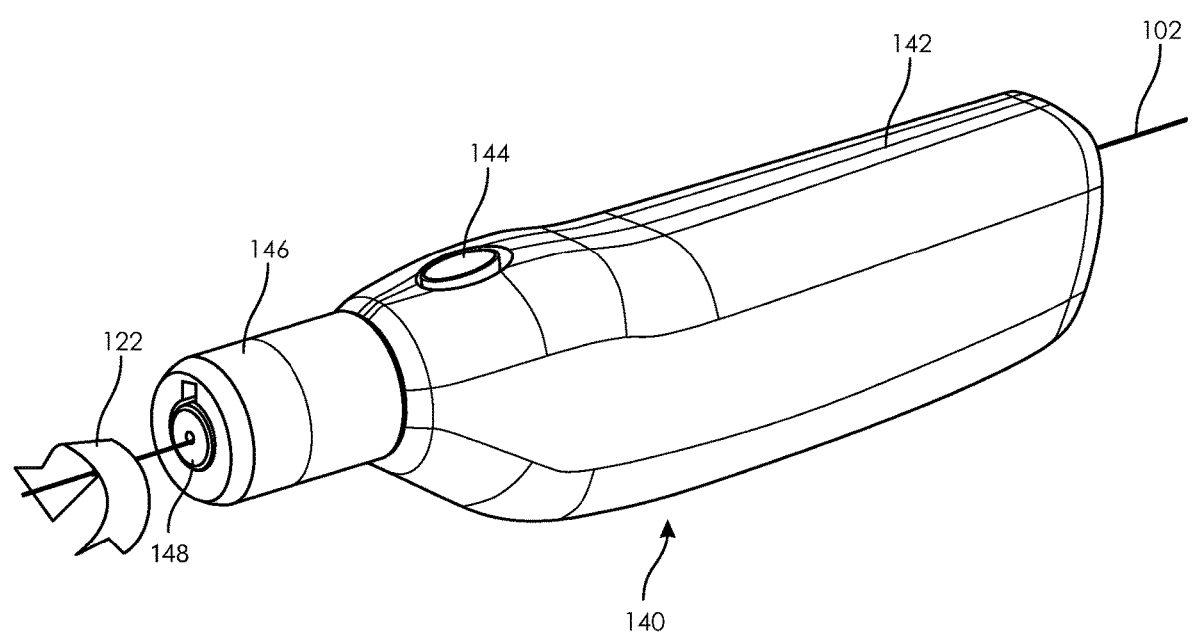
FIG. 10 illustrates a perspective view of a guide-wire manipulation device according to an embodiment of the present disclosure.

FIGS. 8 and 9 illustrate another embodiment of a manual guidewire manipulation device 132 which is generally similar to the previously described devices 100 and 130. However, the device 132 includes a selectively locking thumb roller 134 on a distal end of the device 132. The thumb roller 134 includes a locked mode, seen in FIG. 8, in which the roller 134 is engaged with the guidewire 102, thereby allowing the user to roll the roller 134 and thus the guidewire 102. The thumb roller 134 also includes an unlocked mode, seen in FIG. 9, in which the roller 134 is pulled distally from the casing 136, exposing space 138 and disengaging the roller 134 from the guidewire 102. Thus, in the unlocked mode, the device 132 can be moved along the length of the guidewire 102.

Figure 11:
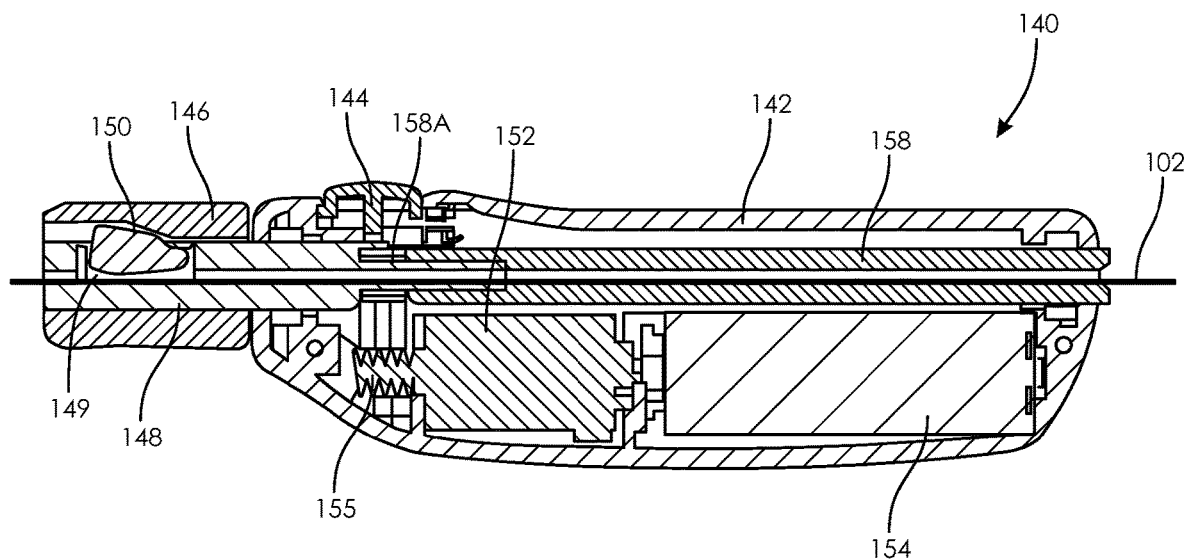
FIG. 11 illustrates a side cross sectional view of the guidewire manipulation device of FIG. 10.
Figure 12:
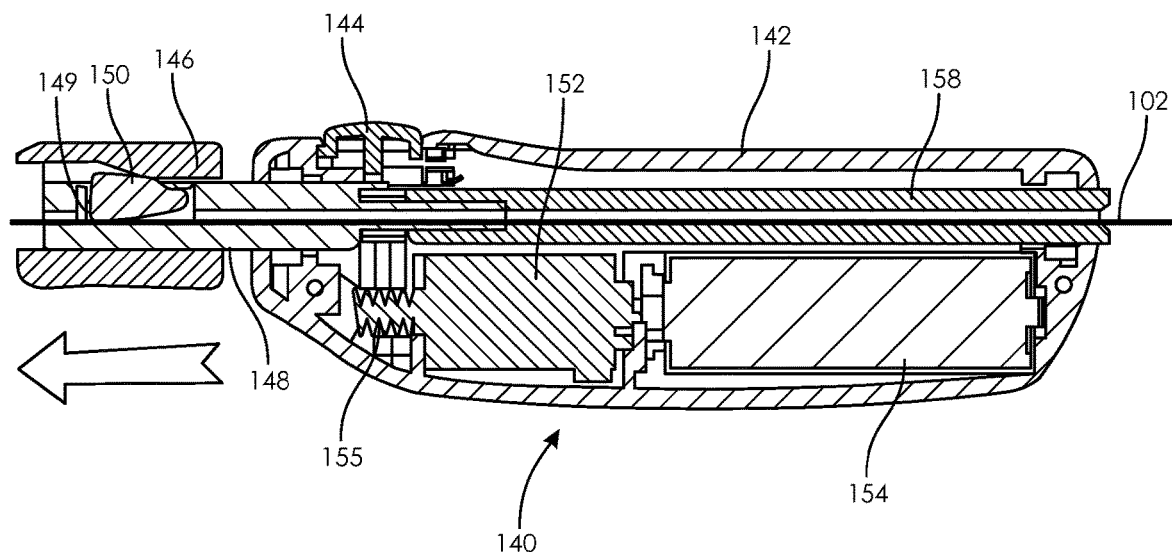
FIG. 12 illustrates a side cross sectional view of the guidewire manipulation device of FIG. 10.
Figure 13:
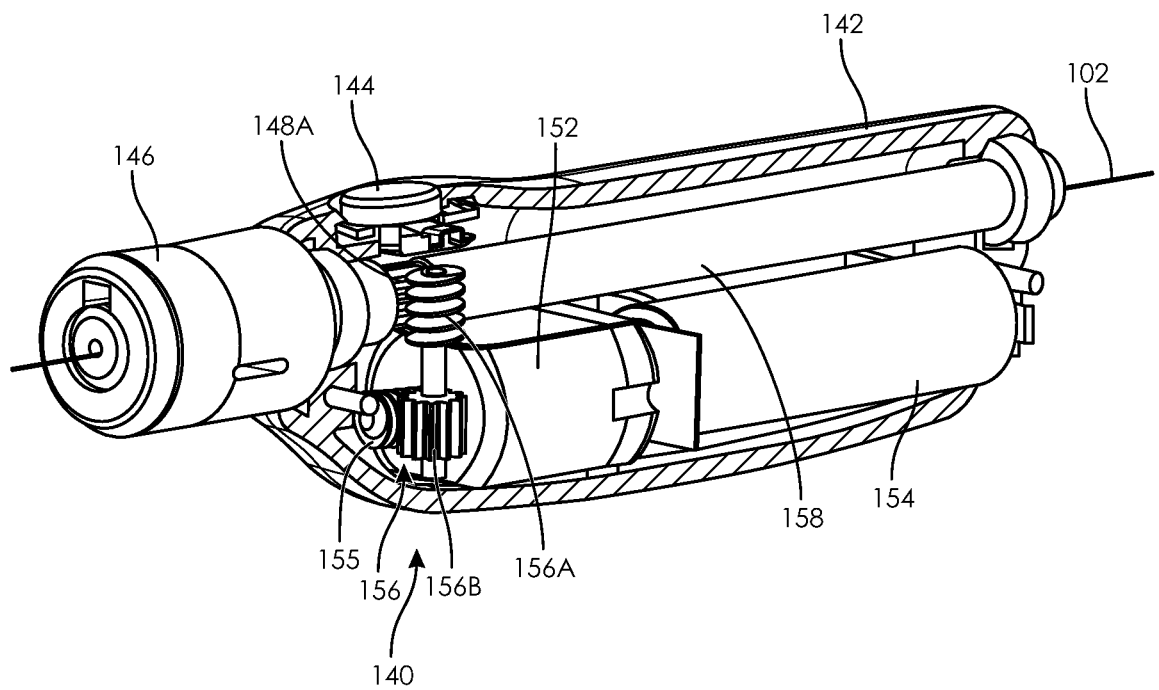
FIG. 13 illustrates a perspective open view of the guide-wire manipulation device of FIG. 10.
Figure 14:
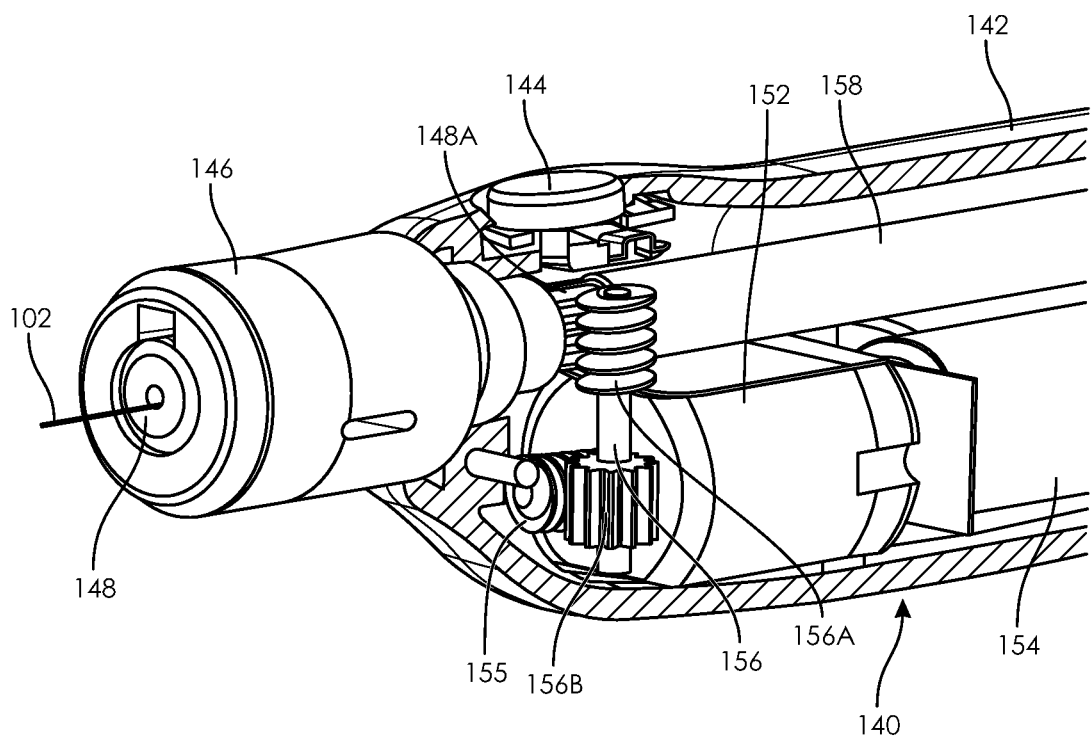
FIG. 14 illustrates a perspective open view of the guide-wire manipulation device of FIG. 10.
Figure 15:
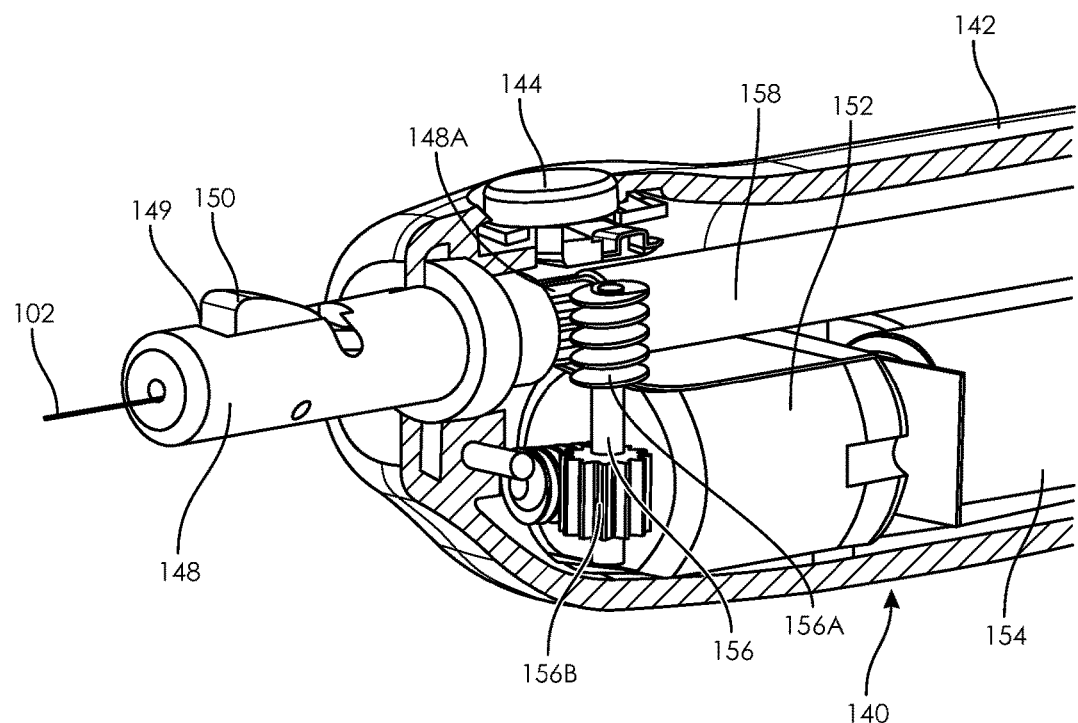
FIG. 15 illustrates a perspective open view of the guide-wire manipulation device of FIG. 10.

FIGS. 10-15 illustrate another embodiment of a guidewire manipulation device 140 according to an embodiment of the present disclosure. The device 140 is generally similar to the previously described device 100. For example, the device 140 includes a hand-held (e.g., configured to be held within a user's hand), ergonomic, outer case 142 and a manipulation button 144. As best seen in FIGS. 11 and 12, the device 140 also includes a motor 152 powered by a battery 154 and a guidewire passage 158 configured for passing the guidewire 102.

Preferably, the device 140 includes a locking assembly in the form of a locking hub 146 (similar to the device 132) which allows the user to selectively lock the guidewire 102 with the device 140. The locking hub 146 allows free movement of the guidewire 102 when positioned near the case 142 (FIG. 11) and locks the guidewire 102 when the hub is pulled away from the case 142 (FIG. 12). The hub 146 includes an interior cavity with a top surface angled downward towards the case 142. Within the interior cavity is a locking wedge 150 which is located within a window 149 of a tube 148 that exposes the guidewire 102. In the unlocked position of FIG. 11, the hub 146 restrains the wedge 150 but does not press down on the wedge 150, thereby allowing the guidewire 102 to slide underneath the wedge 150. In the locked position of FIG. 12, the angled interior surface of the hub 146 forces the wedge downward against the guidewire 102, preventing the guidewire from movement relative to the device 140. A perspective view of the wedge 150 can also be seen in FIG. 15.

As seen in FIGS. 11-15, the motor 152 includes a worm 155 that engages a first gear section 156B of shaft 156. A worm 156A of shaft 158 engages gearing 148A on the outer surface of tube 148. In this respect, when the motor 152 is activated, it ultimately rotates the roller assembly, or tube 148. Thus, the hub 146 must be in a slid-out, locked position to cause the guidewire 102 to rotate.

As with all motorized embodiments described in this specification, the device 140 may also include a microprocessor and memory for storing and executing different rotation sequences (i.e., rotation directions and rotation speeds).

Figure 16:
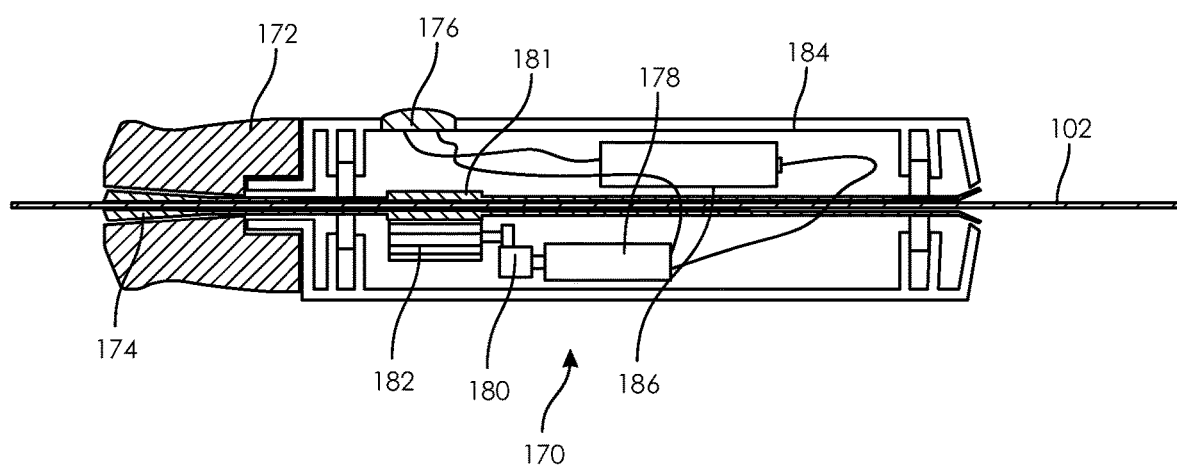
FIG. 16 illustrates a side open view of a guidewire manipulation device according to an embodiment of the present disclosure.
Figure 17:
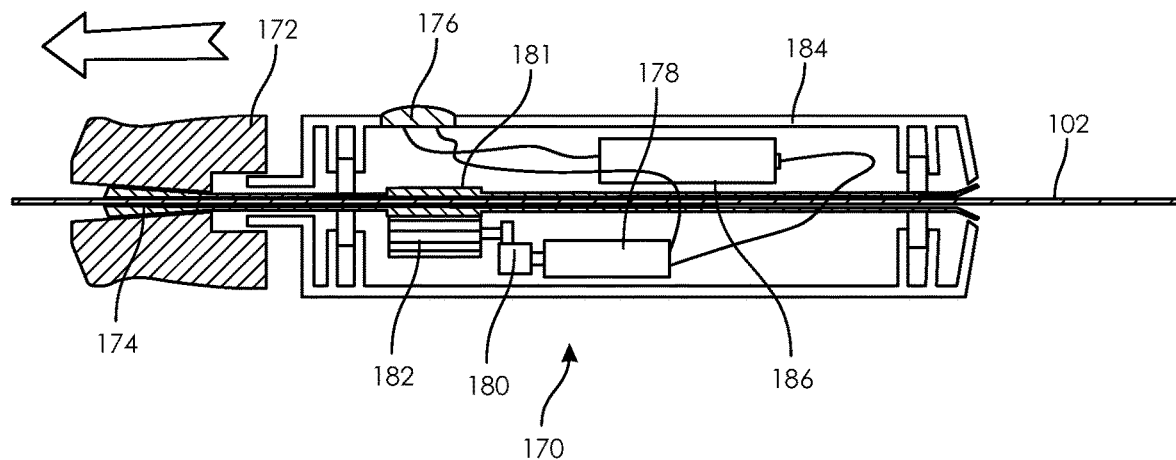
FIG. 17 illustrates a side open view of the guidewire manipulation device of FIG. 16.

FIGS. 16 and 17 illustrate a guidewire manipulation device 170 according to yet another embodiment according to the present disclosure. The device 170 is generally similar to previously described embodiments, including an outer case 184 having an actuation button 176 that is coupled to a battery 186 and a motor 178. The gear 180 of the motor 178 is engaged with a gear 182 that is also engaged with a geared section 181 on wedge tube 174.

A hub 172 includes an interior, angled passage that increases in diameter in a distal direction. The wedge tube 174 is partially positioned within the hub 172. In the unlocked position of FIG. 16, the angled passage of the hub 172 complements a distally expanding shape of the wedge tube 174, thereby preventing the wedge tube 172 from clamping or providing force on the guidewire 102 and thus allowing the guidewire 102 to slide and rotate relative to the device 170. In the looked position of FIG. 17, the hub 172 is moved distally from the case 184, causing the smaller diameter of the interior passage of the hub 172 to wedge or clamp on to the expanded distal end of the wedge tube 174. Thus, the wedge lobe 174 (preferably composed of a compressible, semi-compressible or deformable material) closes around the guidewire 102, maintaining the position of the guidewire 102 relative to the device 170 and further allowing rotation of the guidewire 102.

Figure 18:
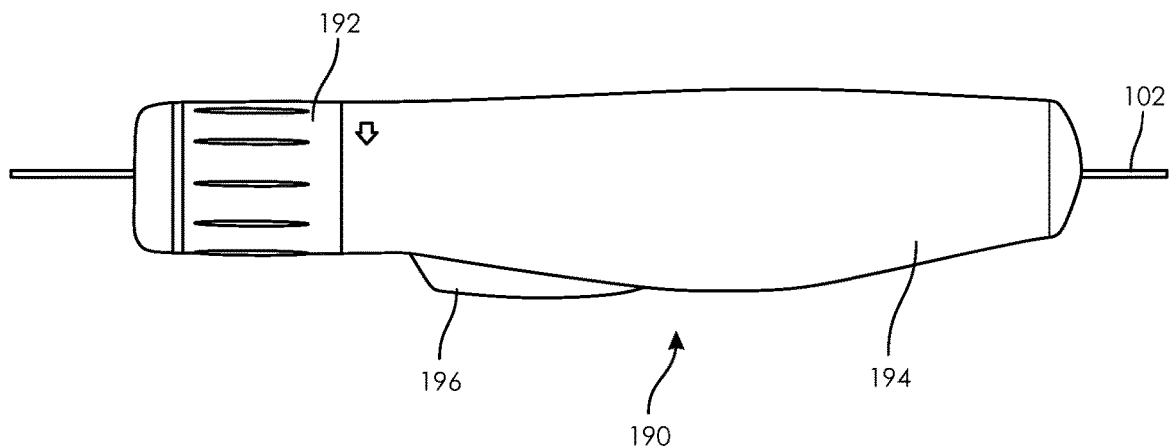
FIG. 18 illustrates a side view of a guidewire manipulation device according to an embodiment of the present disclosure.
Figure 19:
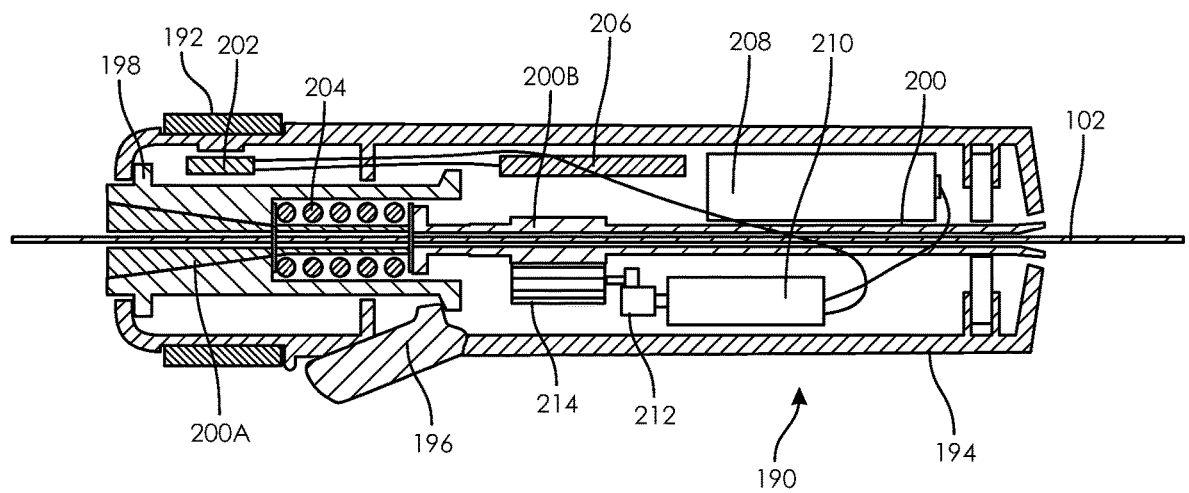
FIG. 19 illustrates a side open view of a guidewire manipulation device according to an embodiment of the present disclosure.
Figure 20:
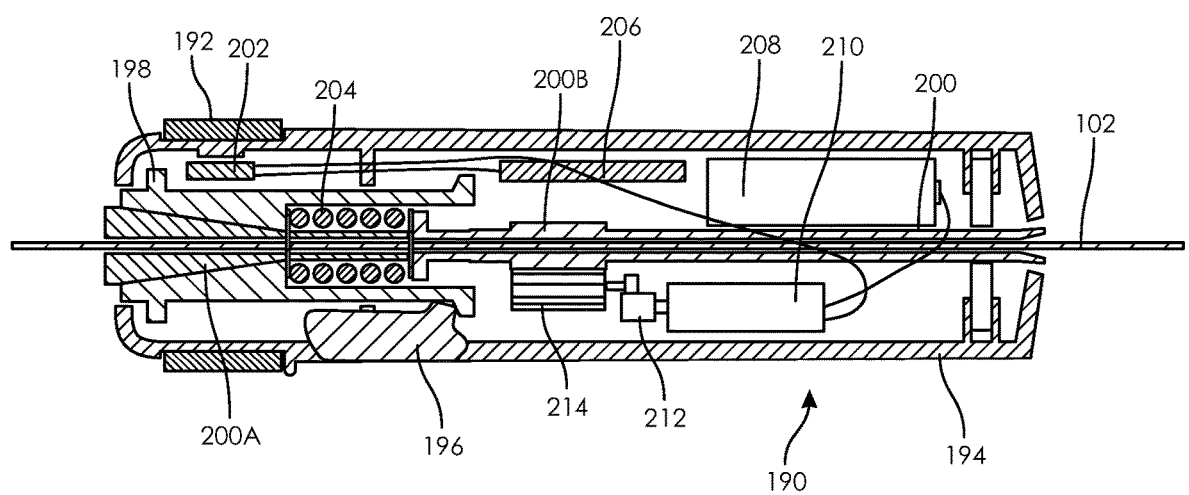
FIG. 20 illustrates a side open view of the guidewire manipulation device of FIG. 19.

FIGS. 18-20 illustrates another embodiment of a device 190 according to the present disclosure. The device 190 is generally similar to the previously described devices. However, the device 190 includes a locking assembly in the form of a guidewire lock activated by depressing a trigger 196. In this respect, the user can rotate hub 192, either clockwise or counter clockwise to respectively rotate the guidewire 102.

The device 190 is generally similar to the previously described embodiments, including a motor 210 powered by a battery 208, a gear 214 coupled to an output gear 212 of the motor 210 and to a geared portion 200B of a wedge tube 200 and a case 194 to contain the components. The motor 210 is controlled by a rocker switch 192 that is connected to a first circuit board 202 which sends the position of the rocker switch 192 to the second circuit board 206. The second circuit board 206 includes a microprocessor and memory for executing a plurality of rotation programs. These rotation programs direct the motor 210 to make predetermined rotation movements such as in a single direction, exponentially increasing rotational speed, quick rotation to cause vibration or a predetermined series of rotational movements. Thus, more complicated movements can be performed by the user.

The device 190 locks on to the guidewire 102 when the user releases trigger 196 (see FIG. 19) and unlocks the guidewire 102 when the user depresses trigger 196. The trigger 196 moves an outer tubing 198 which is biased in a distal direction by a spring 204. The interior passage of the outer tubing 198 increases in diameter in a distal direction forming an inverted cone shape. An inner wedge tube 200 is positioned within the passage of the outer tubing 198 and includes a wedge 200A that increases in size in a distal direction of the device 190. The guidewire 102 is located within a passage of the wedge tube 200.

When the trigger 196 is released, as in FIG. 19, the outer tubing 198 is moved distally by the spring 204, causing the smaller diameter region of the inner passage of the outer tubing 198 to press against the wedge 200A of wedge tube 200. The wedge 200 then compresses around the guidewire 102, locking the guidewire 102 in place relative to the device 190. When the trigger 196 is depressed, as in FIG. 20, a portion of the trigger 196 pushes the outer tubing 198 in a proximal direction, against the bias of the spring 204. The angled portions of the inner passage of the outer tubing 198 move away from the wedge 200a, allowing the inner passage of the wedge tube 200 to release the guidewire 102. Thus, the user can selectively lock on to and rotate the guidewire 102 (with the roller assembly, including wedge tube 200) by releasing the trigger 196 and pressing the actuation button 192.

Figure 21:
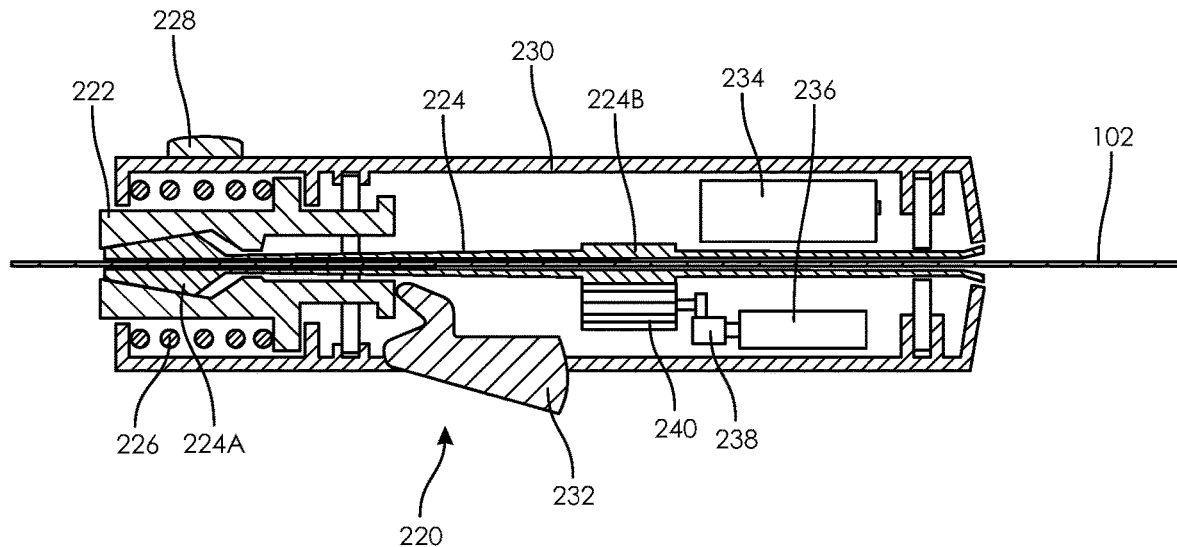
FIG. 21 illustrates a side open view of a guidewire manipulation device according to an embodiment of the present disclosure.
Figure 22:
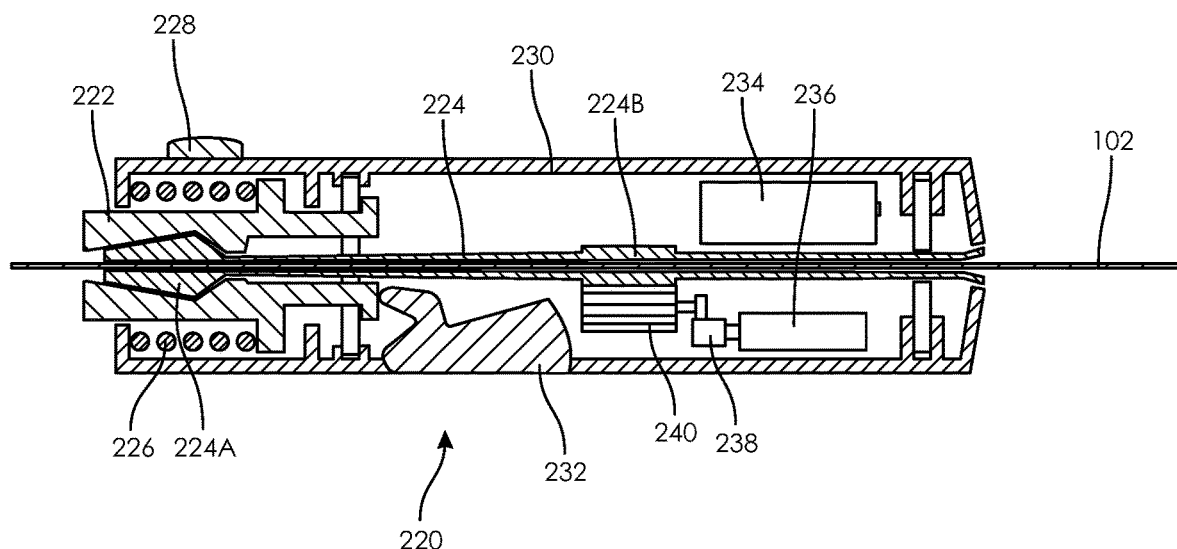
FIG. 22 illustrates a side open view of the guidewire manipulation device of FIG. 21.

FIGS. 21 and 22 illustrate another embodiment of a guidewire manipulation device 220 according to the present disclosure. The device 220 is generally similar to the previously described embodiments. Including a battery 234 powering a motor 236 which drives a wedge tube 224 (via a gear 240 connected to geared region 224B and output gear 238) and an actuation button 228.

The device 220 further includes a locking mechanism assembly that locks the lateral position of the guidewire 102. As seen in FIG. 21, when the user releases the trigger 232, the device remains in a locked position, allowing the user to rotate the guidewire 102. As seen in FIG. 22, when the user depresses the trigger 232, the device remains in an unlocked position, allowing the user to slide the device 220 along the guidewire 102 and preventing guidewire rotation.

In the locked position, the trigger 232 maintains an outer tube 222 in a proximal position, proximally biased by a spring 226. The outer tube includes an inner passage that generally decreases in diameter in a distal direction. The inner surface of the outer tube 222 presses against a wedge portion 224A of a wedge tube 224, causing the wedge tube 224 to press against and lock onto the guidewire 102.

In the unlocked position, the trigger 232 pushes the outer tube 222 distally, against the bias of the spring 226. The surface of the inner passage of the outer tube 222 moves away from the wedge 224A, releasing the wedge tube 224 from the guidewire 102.

The systems and methods disclosed herein further comprise a guidewire manipulation device for selectively imparting motive force (rotational and/or axial/longitudinal (linear) motion) to a guidewire. In use, such a guidewire manipulation device is selectively locked to a guidewire and is activated to impart motive force to maneuver the guidewire to a desired location during an endovascular procedure. The motive force applied to the guidewire is selectively rotational or axial to facilitate moving the guidewire through a vessel and/or penetrating occlusions.

Figure 23:
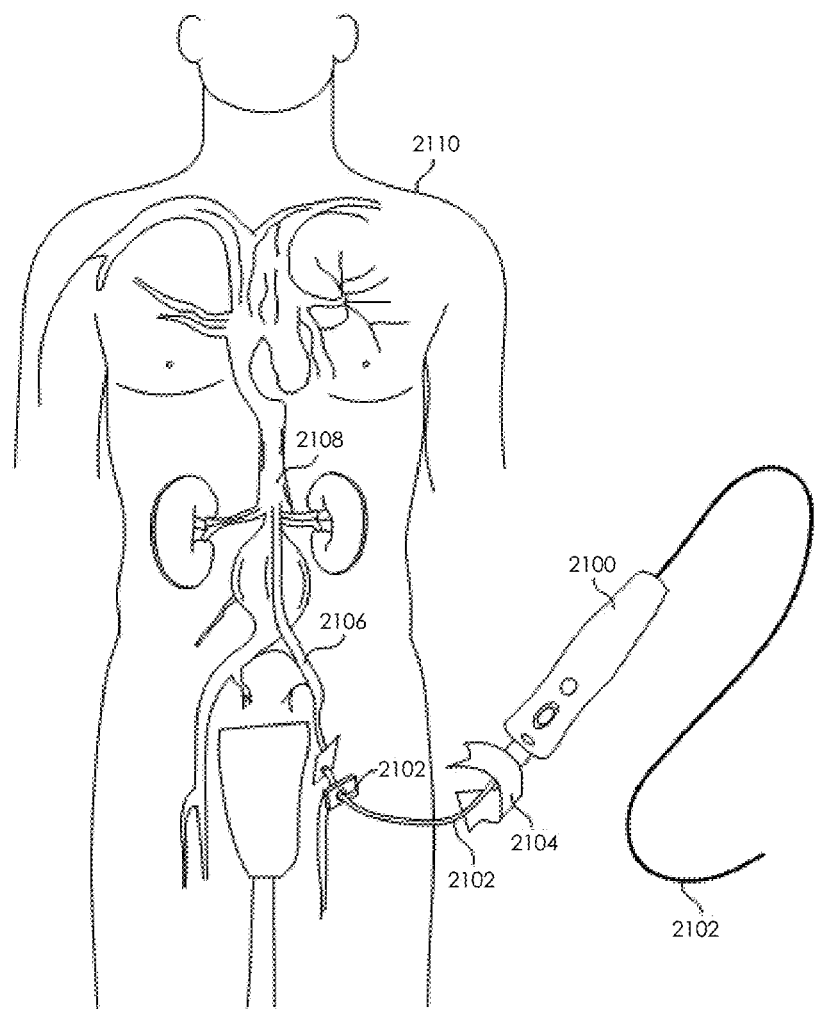
FIG. 23 illustrates a view of one embodiment of a guidewire manipulation device being used on a patient according to an embodiment of the present disclosure.

FIG. 23 illustrates a view of a guidewire manipulation device 2100 being used on a patient 2110 according to one embodiment of the present disclosure. In one embodiment, the guidewire manipulation device 2100 is a handheld device capable of fitting in the palm of a user's hand and being operated using one hand. In one embodiment, the guidewire manipulation device 2100 is advanced over a guidewire 2102, i.e., the guidewire 2102 passes through a longitudinally oriented passage in the device 2100. During an endovascular procedure, the guidewire 2102 is introduced into a vessel 2106 (e.g., a femoral artery) of the patient 2110. The guidewire manipulation device 2100 is selectively locked to the guidewire 2102. As the guidewire is advanced into the patient, the user operates the manipulation device 2100 to impart motive force (rotational and/or axial motion) to the guidewire 2102, as appropriate.

For example, as a distal end 2108 of the guidewire 2102 reaches an angled, curved, stenosed, or occluded region of the vessel 2106, the user locks the manipulation device 2100 to the guidewire and imparts rotational motive force to the guidewire 2102 (e.g., in a counter-clockwise direction indicated by arrow 2104), thereby causing the distal end 2108 of the guidewire 2102 to more easily advance through the angled, curved, stenosed, or occluded region of the vessel 2106. Once advanced past the region, the device 2100 is unlocked from the guidewire and the guidewire can be further advanced through the vessel. In another example, the distal end 2108 of the guidewire 2102 reaches an obstruction (e.g., an embolism, including, but not limited to a thromboembolism) but is unable to pass the obstruction. The user then locks the guidewire manipulation device 2100 to the guidewire 2102 and imparts a vibratory motion (e.g., rapidly oscillating between clockwise and counter-clockwise rotation). Such motion causes the distal end 2108 of the guidewire 2102 to pass through the obstruction. In another example, when the distal end 2108 of the guidewire 2102 reaches an obstruction, the user locks the guidewire manipulation device 2100 to the guidewire 2102 and imparts an axial motion (e.g., a linear movement of the guidewire 2102) to create a jackhammer effect. In another embodiment, the user may lock the device 2100 to the guidewire 2102 and simultaneously impart both rotational and axial motion to the guidewire 2102. In another embodiment of the present disclosure, a sequence of predefined guidewire manipulations (i.e., a pattern) may be produced using a computer program for controlling the motion as described in detail below. Various motive patterns to be selectively used in various surgical situations can be selected from memory and applied to the guidewire.

Figure 24:
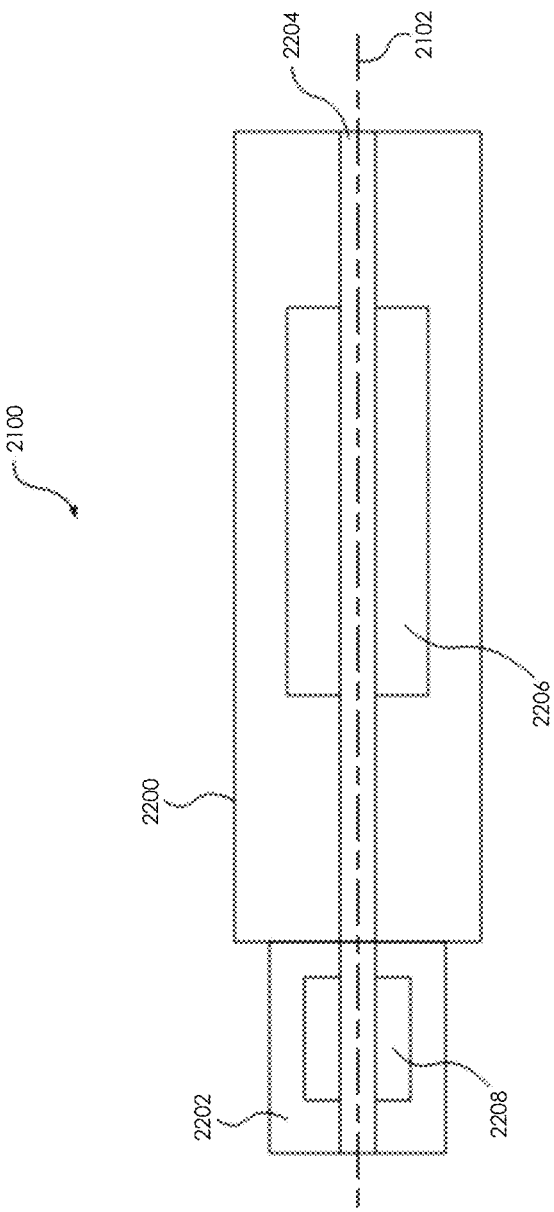
FIG. 24 depicts a schematic block diagram of a guidewire manipulation device according to an embodiment of the present disclosure.

FIG. 24 depicts a schematic block diagram of one embodiment of a guidewire manipulation device 2100. The guidewire manipulation device 2100 defines an axially longitudinal passage 2204 through which the guidewire 2102 is threaded during use. The guidewire manipulation device 2100 comprises a housing 2200, an actuator 2206, and a chuck 2202. The chuck 2202 comprises a guidewire locking mechanism 2208. During use, the chuck 2202 is locked to the guidewire 2102 using the looking mechanism 2208. Once locked, the actuator selectively imparts motive force (rotational motion and/or axial motion) to the guidewire 2102.

Figure 25:
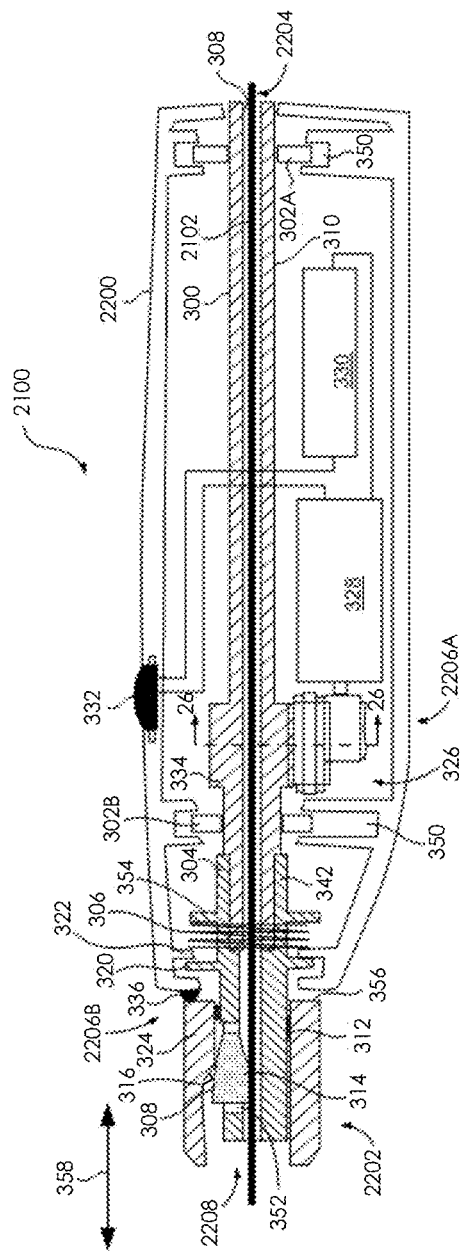
FIG. 25 depicts a vertical cross-sectional view of a guidewire manipulation device according to an embodiment of the present disclosure.

FIG. 25 depicts a vertical cross-sectional view of one embodiment of a guidewire manipulation device 2100. In this embodiment, the actuator 2206 of FIG. 24 is divided into a rotary actuator 2206A and an axial actuator 2206B such that the device may selectively apply to the guidewire: no motive force, rotary motive force or rotary and axial motive force.

Device 2100 comprises a housing 2200 typically formed into halves that are glued, bonded, screwed, or otherwise affixed to each other to form an enclosure. Within the housing 2200 are defined slots 350 wherein are retained bushings 302A and 302B. The bushings 302A and 302B support an axle 300 on its outer surface 310. The axle 300 defines the passage 2204 extending axially through the axle 300. When in use, the guidewire 2102 is threaded through the passage 2204.

The rotary actuator 2206A comprises the axle 300, a motor 328, a drive assembly 326, a controller 330, and a control switch 332. The drive assembly 326 couples rotational motion of the motor 328 to the axle 300 using a plurality of gears, further described with respect to FIG. 26 below. In one embodiment of the present disclosure, the controller 330 is simply one or more batteries that are coupled to the motor 328 via the control switch 332. In such an embodiment, the control switch 332 may simply apply a voltage from the one or more batteries to the motor 328 to cause the motor 328 to rotate. In its simplest form, the control switch 332 is a simple single-pole, single-throw (SPST), momentary contact switch. In other embodiments, the controller 330 comprises a programmable microcontroller as described with respect to FIG. 28 below. In other embodiments, the switch 332 may apply voltage to cause the motor 328 to selectively rotate clockwise or counter-clockwise. The control switch 332 is generally mounted to be exposed to the exterior of the housing 2200 and facilitate manipulation by one hand of a user (e.g., a thumb activated push-button or slide switch).

The axle 300 is coupled to a chuck 2202. In one embodiment, the chuck 2202 comprises a coupler 304, a hub 324 and a wedge 314. The coupler 304 and the axle 300 have splined mating surfaces 342 for coupling the rotational motion of the axle 300 to the chuck 2202, while allowing the coupler 304 to move in an axial direction. The hub 324 is threaded onto the coupler 304 at surface 312. The wedge 314 is located in a window 352 defined by the coupler 304. The hub 324 retains the wedge 314 within the window 352. In a disengaged (unlocked) position, the hub 324 does not impart pressure to the wedge 314 thereby allowing the guidewire 2102 to slide freely beneath the wedge 314 and through the passage 2204. To lock (engage) the guidewire into the lock mechanism 2208, the hub 324 is rotated relative to the coupler 304 such that the angled surface 316 of the hub 324 interacts with the top surface 308 of the wedge 314. As the hub 324 is moved relative to the coupler 304 via the mating threaded surfaces 312, the wedge 314 is forced against the guidewire 2102. Consequently, the guidewire 2102 is captured between the wedge 314 and the coupler 304 and thereby locked into the chuck 2202. Once locked, any motion of the chuck 2202 (e.g., rotational and/or longitudinal) is imparted as motive force to the guidewire 2102.

Other embodiments of the present disclosure utilize other forms of chucks. In a broad sense, any mechanism that can be used to selectively lock the guidewire to a source of motive force may be used. Other forms of chucks having multiple jaws or compressive slotted cylinders are applicable.

The coupler 304 comprises a spring seat 354 supporting a first end of a spring 306. The second end of spring 306 rests against a flange 322 that extends from the inner surface of the housing 2200. The spring 306 is one embodiment of a resilient member that biases the coupler 304 inwardly toward the axle 300. The coupler 304 further comprises a flange 320 that extends radially from the outer surface of the coupler 304. The flange 320 is positioned along the coupler 304 to limit the amount of axial movement that can be imparted to the chuck 2202. The flange 320 abuts the housing flange 322. As such, the spring 306 biases the coupler 304 to maintain contact between the flange 320 and the flange 322.

To impart axial (longitudinal) motion to the chuck 2202, the bottom surface 356 of the hub 324 is dimpled. The surface 356 interacts with a protrusion 336 extending from the exterior surface of the housing 2200 proximate the surface 356 of the hub 324. Depending on the position of the hub 324 relative to the coupler 304, the spring 306 insures that the protrusion 336 interacts with the dimpled surface 356. Upon locking the chuck 2202 to the guidewire 2102 and imparting rotation to the chuck 2202, the guidewire 2102 moves in an axial direction as indicated by arrow 358. To disengage the axial motive force, the hub 324 is rotated relative to the coupler 304 along the threads 312 to decouple the protrusion 336 from the surface 356. In this manner, the locking mechanism 2208 retains the guidewire 2102 such that rotational motion of the axle 300 is imparted to the guidewire 2102 without imparting axial motion. In this embodiment, the axial motion actuator 2206B comprises the hub 324, spring 306, coupler 304 and the housing 2200.

Figure 26:
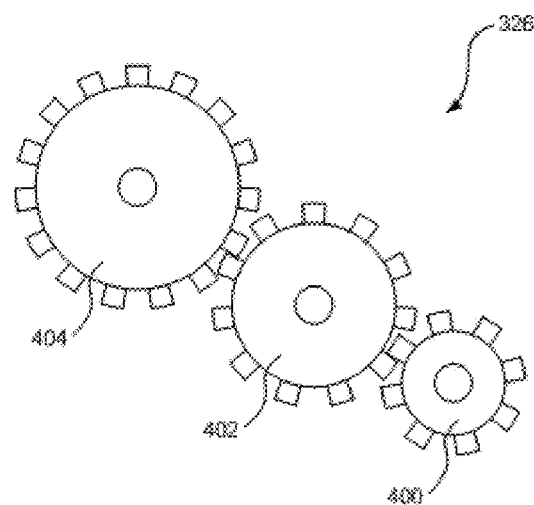
FIG. 26 depicts a portion of an actuator used in the guidewire manipulation device of FIG. 25.

FIG. 26 depicts a cross sectional view of the drive assembly 326 of the rotary actuator 2206A taken along line 26-26 of FIG. 25 in accordance with one embodiment of the present disclosure. The drive assembly 326 comprises a motor gear 400, an intermediary gear 402 and an axle gear 404. The motor 328 of FIG. 25 is coupled to the motor gear 400 to impart rotational motion to the motor gear 400. In one embodiment, the axle gear 404 is formed as an integral part of this surface of the axle 300 of FIG. 25. The intermediary gear 402 is designed to provide a gear ratio between the motor gear 400 and axle gear 404. The diameters and the number of teeth of each gear is considered to be a design choice that will define the speed of rotational motion of the guidewire 2102 as well as the oscillatory speed of the axial motion.

In other embodiments, the motor 328 of FIG. 25 may be coupled to the axle via other forms of drive assemblies, e.g., direct drive, worm gear, and/or the like. The specific motor and drive assembly characteristics are considered a design choice to develop specific guidewire rotation speed and torque. In some embodiments, the drive assembly may be adjustable to facilitate creating specific speed and torque profiles or adjustments. One form of adjustments may be facilitated by the use of a stepper motor that can be controlled with a pulse width modulated signal produced by the controller, as discussed below.

An alternative embodiment for imparting rotary motive force in selectable directions uses a gear train comprising two larger diameter spur gears mounted on a common shaft that is driven constantly in one direction by an electric motor. Each of the two spur gears has a section of its teeth, something over ½ its total number, removed. The removed sections of teeth are positioned such that only one or the other of two additional smaller spur gears, each located to be driven by one of these common shaft gears, will be driven at a time. The two smaller spur gears are then used one at a time to drive the gear on the axle, but the positioning of one additional gear between just one of these driving gears and the axle gear results in the rotational direction of the axle being reversed when that set is driving the axle gear.

Another embodiment, if only forward and reverse is required without a near constant rotational speed in either direction, has the spur gear on the axle driven by a pivoted ¼ pie-shaped plate. The toothed curved section opposite the pivot near the tip would be configured to have the correct pitch radius to mesh with the axle spur gear. This pivoted gear section plate would have, running upwards from its pivot, a slot in its face in which a pin, mounted off-center and a disc, could slide up and down freely. As an electric motor turns this disc in a constant direction, it would cause the pivoted plate to wobble back and forth so that its gear section drives the axle spur gear in one direction and then in the reverse direction.

Figure 27:
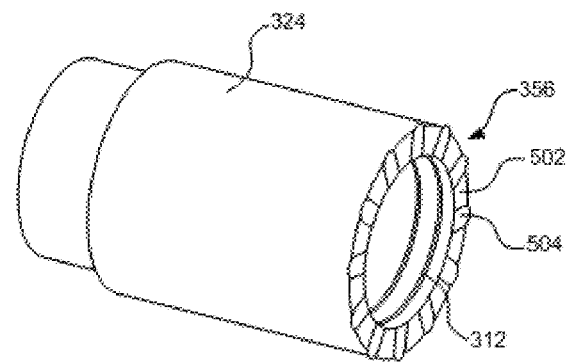
FIG. 27 depicts a perspective view of a hub of a chuck that imparts axial motive force to a guidewire when using the guidewire manipulation divisive FIG. 25.

FIG. 27 depicts a perspective view of the hub 324 in accordance with one embodiment of the present disclosure. The hub 324 comprises a surface 356 having a plurality of dimples 504 and spaces 502 between the dimples 504. The hub 324 further comprises a threaded interior surface 312. The threaded interior surface 312 is adapted to interact with a threaded exterior surface of the coupler 304 to adjust the position of the hub relative to the coupler 304 and the wedge 314. The dimples 504 and the spaces 502 between the dimples 504 are adapted to interact with the protrusion 336 to impart axial motion to the chuck 2202. The spacing of the dimples and the speed of the motor control the oscillation rate of the axial motion. Furthermore, the depth of the dimples 504 relative to the spaces 502 on the surface 356 controls the travel distance of the axial motion.

Figure 28:
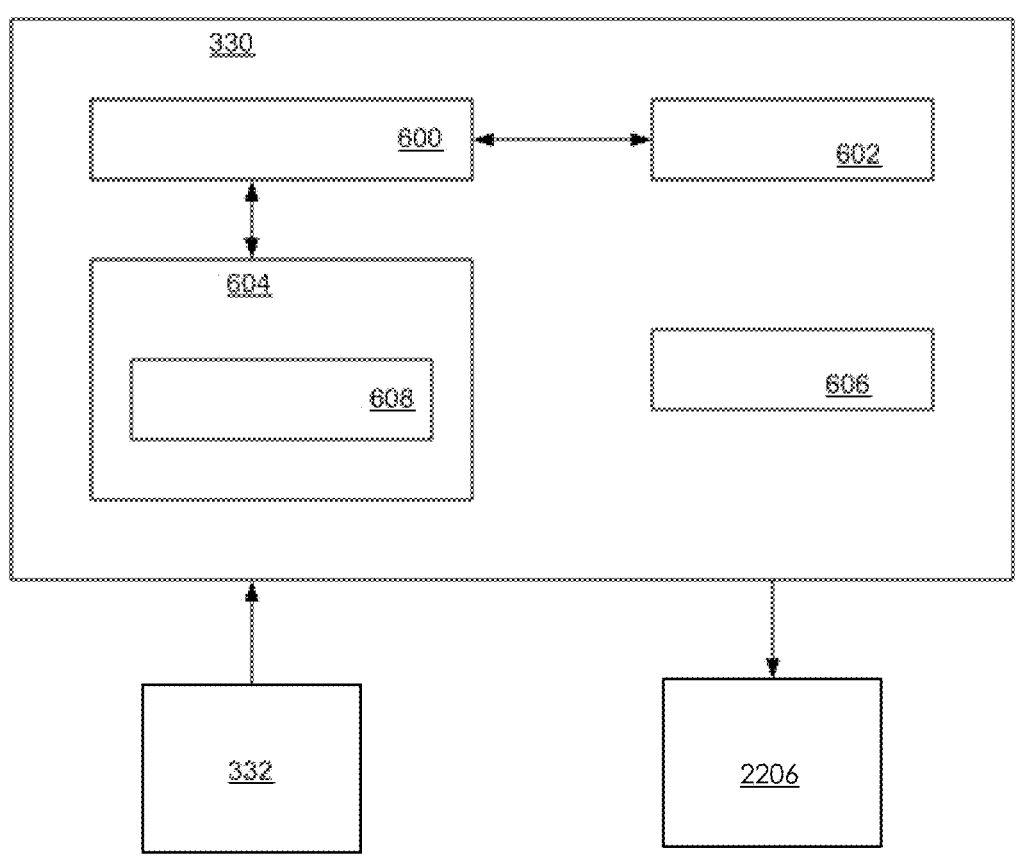
FIG. 28 depicts a block diagram of a controller for a guidewire manipulation device in accordance with an embodiment of the present disclosure.

FIG. 28 depicts a block diagram of the controller 330 in accordance with one embodiment of the present disclosure. The controller 330 comprises a microcontroller 600, support circuits 602, memory 604 and a power supply 606. The microcontroller 600 may be one or more of many commercially available microcontrollers, microprocessors, application specific integrated circuits (ASIC), and the like. The support circuits 602 comprise well known circuits that facilitate the operation of the microcontroller 600 including, but not limited to, clock circuits, cache, power supplies, input/output circuits, indicators, sensors, and/or the like. In one embodiment, the power supply 606 comprises one or more batteries. In other embodiments, the power supply 606 may comprise an AC to DC converter to allow the guidewire manipulation device to be plugged into a wall socket. In further embodiments, the power supply 606 may comprise one or more batteries and a charging circuit for the batteries may be inductively coupled to a base charger.

The memory 604 may be any form of memory device used to store digital instructions for the microcontroller 600 as well as data. In one embodiment, the memory 604 is random access memory or read only memory comprising control code 608 (e.g., computer readable instructions) that are used to control the actuator 2206 to impart motion to the guidewire 2102. The programs utilized by the microcontroller 600 to control the actuator 2206 are generally controlled by the control switch 332 and/or another input device.

In one embodiment of the present disclosure, the motor 328 is a stepper motor that is controlled using, for example, a pulse width modulated signal produced by the controller 330 to impart specific torque and/or speed profiles to the motor 328. In some embodiments, predefined programs can be generated and selected through manipulation of the switch 332 to enable a user to overcome specific types of obstructions within the path of the guidewire. For example, if a surgeon encounters a specific type of embolism, a specific program defining the motion of the guidewire to overcome the obstruction can be selected and implemented. Various programs can be generated through empirical study of guidewire utilization in endovascular procedures. To select a particular motion pattern, the switch may be a slide switch having a plurality of selectable positions, where each position corresponds to a different motion pattern.

Figure 29:
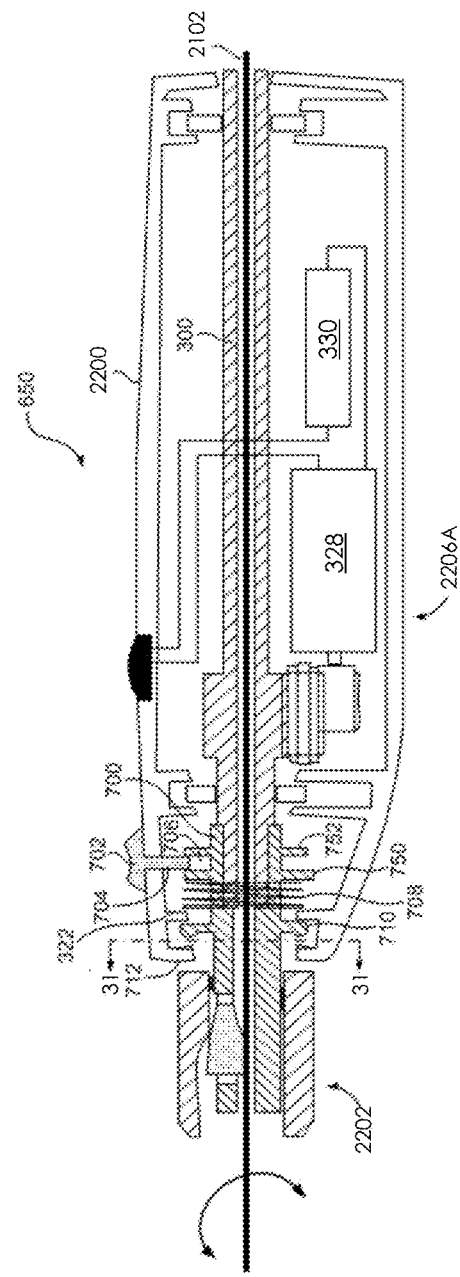
FIG. 29 depicts a vertical cross-sectional view of alternative embodiment of the guidewire manipulation device.

FIG. 29 depicts a vertical cross-sectional view of a guidewire manipulation device 650 according to an alternative embodiment of the present disclosure. In this embodiment, the use of axial motion is selected through manipulation of a mechanical switch 702. As with the prior embodiment, this embodiment selectively imparts to a guidewire: no motive force, rotary motive force, or rotary and axial motive force. The device 650 comprises a rotational actuator 2206A as described above with respect to FIG. 25. In this embodiment, a coupler 700 comprises a spring seat 750, a dimpled flange 710 and a switch stop 752. A slidable switch 702 comprises an extension 704 that interacts with a switch seat 752. The switch seat 752 and the spring seat 750 define a space 706 that captures the switch extension 704. Manipulation of the switch 702 causes the coupler 700 to move axially along the surface that mates with the axle 300. A spring 708 is positioned between the spring seat 750 and the housing flange 322. The spring 708 biases the coupler 700 inwardly toward the axle 300. The dimpled flange 710 radially extends from the coupler 700. One surface of the dimpled flange 710 abuts the housing flange 322 to limit the distance the coupler 700 moves in an axial direction. The dimpled flange 710 has a surface aligned with a dimpled surface 712 of the housing 2200. When the guidewire 2102 is locked to the chuck 2202 and the rotational actuator 2206A is activated, the guidewire 2102 rotates without any axial movement. As described further with respect to FIG. 32 below, when the switch 702 is moved forward to cause the dimpled surface of flange 710 to engage the dimpled surface 712, the guidewire 2102 axial motive force is imparted to the guidewire 2102.

Figure 30:
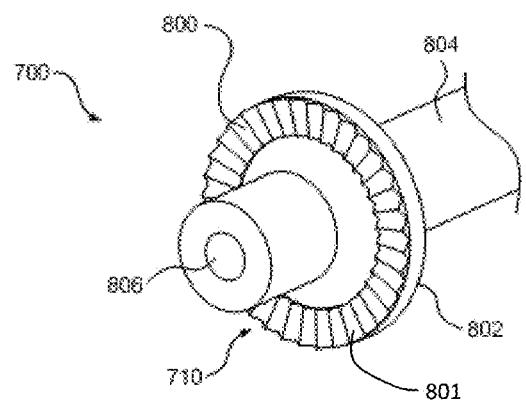
FIG. 30 depicts a partial perspective view of a portion of a guidewire drive assembly for the guidewire manipulation device of FIG. 29.

FIG. 30 depicts a partial perspective view of the coupler 700 in accordance with one embodiment of the present disclosure. The coupler 700 has an aperture 806 through which the guidewire 2102 is threaded. The dimpled flange 710 comprises a radially extending flange 802 having a plurality of dimples 800 formed in the surface 801. In one embodiment, the dimples 800 are formed as a sequence of wedges. In other embodiments, to cause axial motion of the chuck when the coupler 700 is rotated, the surface 801 of the flange 802 is varied such that interaction with a corresponding surface causes axial movement of the coupler 700.

Figure 31:
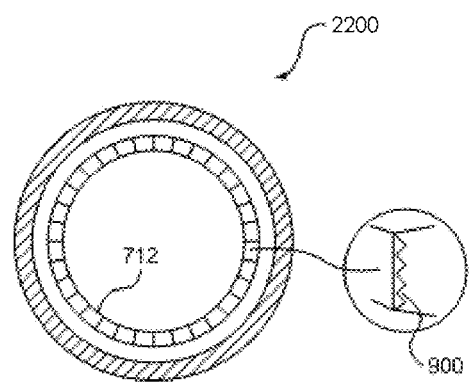
FIG. 31 depicts a cross-sectional view of a portion of the housing for the guidewire manipulation device of FIG. 29.

FIG. 31 depicts a cross-sectional view of the housing 2200 taken along line 31-31 in FIG. 29. In one embodiment, the surface 712 comprises corresponding protrusions shaped to interact with the dimples 800 in the surface 801 of the coupler 700. In another embodiment, the surface 712 may comprise complementary wedges 900 to the surface 801 of the coupler 700. The shape of the wedges 900 defines, in part, the distance travelled, the rate of acceleration of the guidewire 2102, and the speed of the oscillation of the guidewire 2102.

Figure 32:
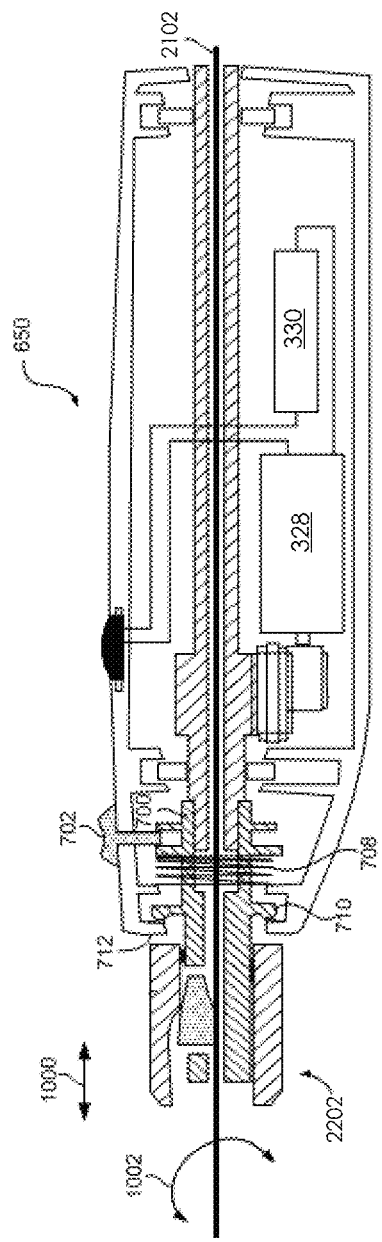
FIG. 32 depicts a vertical cross-sectional view of the guidewire manipulation device of FIG. 29 having the actuator engaged to apply axial motive force to the guidewire in accordance with one embodiment of the present disclosure.

FIG. 32 depicts an embodiment of the guidewire manipulation device 650 of FIG. 29 where the dimpled flange 710 has been engaged the protrusion surface 712. In this manner, the switch 702 has moved the coupler 700 forward to facilitate engagement of the surfaces 710 and 712. When the chuck 2202 locks to the guidewire 2102 and the rotary actuator is activated, the guidewire 2102 rotates as shown in arrow 1002 and axially oscillates as represented by arrow 1000.

Figure 33:
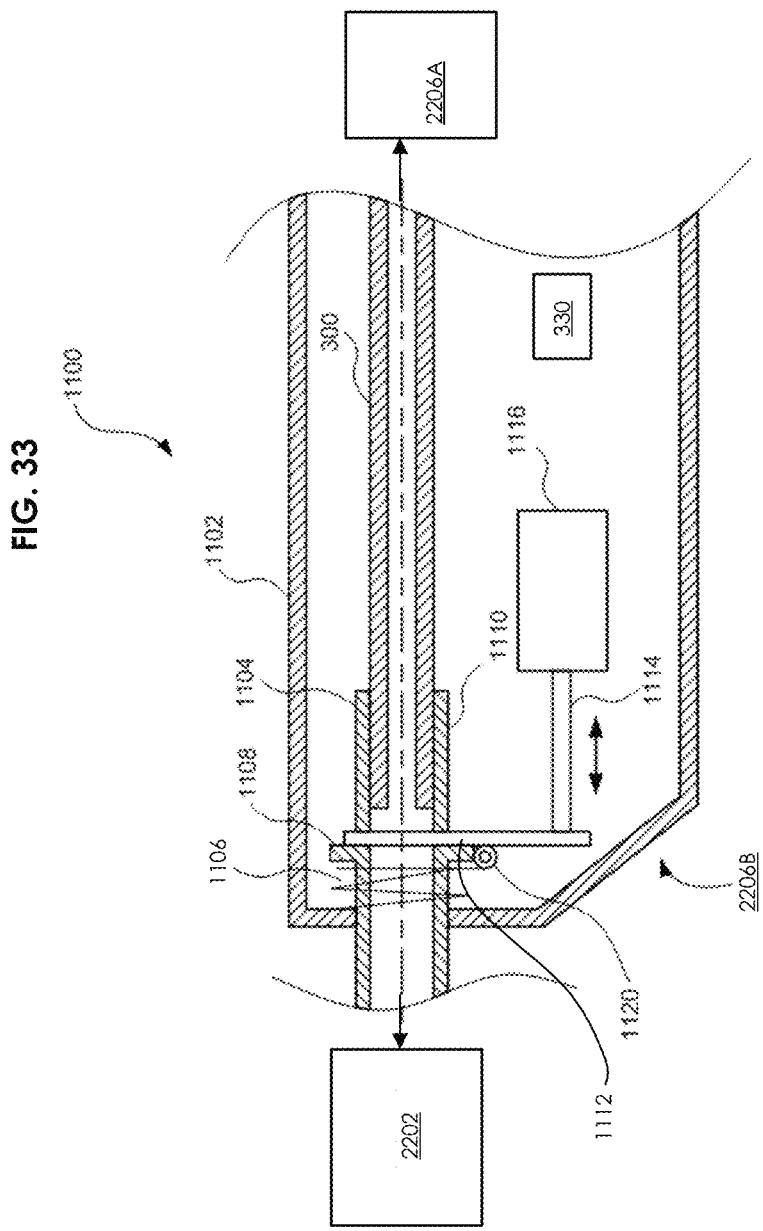
FIG. 33 depicts a partial, vertical cross-sectional view of another embodiment of a guidewire manipulation device for imparting axial motive force to a guidewire.

FIG. 33 depicts a vertical cross-sectional view of a portion of a guidewire manipulation device 1100. Device 1100 comprises an axial actuator 2206B that can be selectively utilized without imparting rotational motion of the guidewire. As such, with this embodiment, the device 1100 selectively imparts to the guide wire: no motive force, rotary motive force, axial motive force, or axial and rotary motive force.

In one embodiment, the device 1100 comprises a linear actuator 1116 coupled to a shaft 1114 that interacts with a fulcrum 1112. The linear actuator 1116 imparts linear motion to one portion of the fulcrum 1112. The fulcrum is mounted upon a pivot point 1120 such that the fulcrum 1112 rotates about the pivot point 1120 as a linear motive force is applied to the fulcrum 1112. A second end of the fulcrum 1112 interacts with a coupler 1104. The coupler 1104, as with prior embodiments, has a splined surface that interacts with the axle 300 to impart rotational motion to the coupler 1104, as needed. The coupler 1104 comprises a spring seat 1108. A spring 1106 is positioned between the housing 1102 and the spring seat 1108 to bias the coupler 1104 toward the axle 300. The fulcrum 1112 couples to the spring seat 1108 such that motion of the fulcrum 1112 axially moves the coupler 1104. In this manner, without any rotational motion the linear actuator 1116 imparts axial motion to the coupler 1104 and to guidewire 2102 locked in the chuck 2202.

In one embodiment, the linear actuator 1116 may be a solenoid, piezoelectric actuator, linear motor, rotary motor and ball screw or rack/pinion, and/or the like. In another embodiment, a hammer-drill type assembly may be used to impart axial force to the guidewire.

The controller 330 in a manner similar to that described for controlling the motor 328 of FIG. 25 may control the linear actuator 1116.

Figure 34:
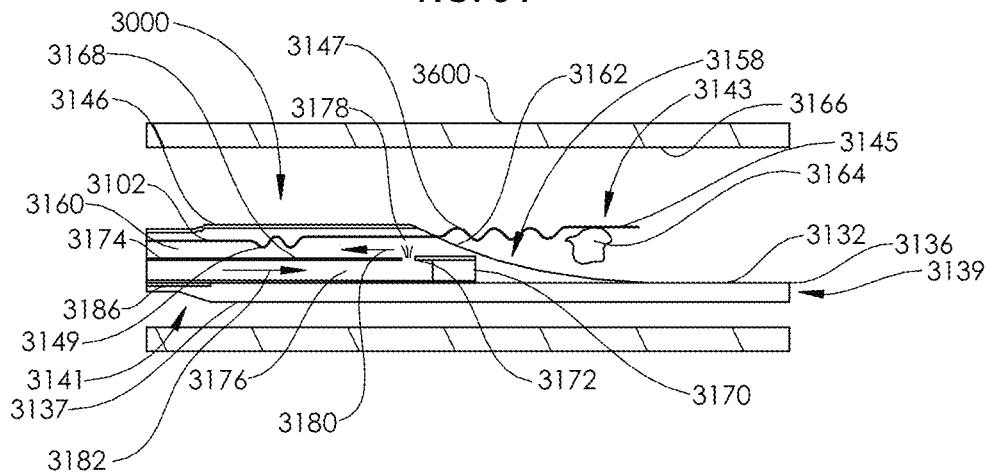
FIG. 34 illustrates an aspiration catheter within a blood vessel being used in conjunction with a guidewire which is moved by a guidewire manipulation device, according to an embodiment of the present disclosure.

FIG. 34 shows an open distal end 3158 of an aspiration lumen 3160 of an aspiration catheter 3000 for aspirating thrombus within a blood vessel 3600. A skive 3162 may be formed in a polymer jacket 3146 of the aspiration catheter 3000, to aid entry of a thrombus 3164 that is aspirated into the aspiration lumen 3160 (in the direction of arrow 3180) by the combination of the vacuum created by a vacuum source (e.g., VacLok® Syringe, vacuum bottle) and the injection of fluid into the distal end of the aspiration lumen 3160, as described below. The skive 3162 also minimizes the chances of the open distal end 3158 being sucked against a blood vessel wall 3166. A distal supply tube 3168 of the aspiration catheter 3000 has a closed distal end 3170. For example, it may be occluded during manufacture using adhesive, epoxy, hot melt adhesive or an interference member, such as a metallic or polymeric plug. However, in some embodiments, the aspiration catheter 3000 may have a blunt or non-angled tip, instead of the skive 3162. Alternatively, the distal supply tube 3168 may be closed off by melting a portion of it. The distal supply tube 3168 has a lumen 3176 extending its length and an orifice 3172 formed through its wall 3174 at a location adjacent and proximal to the closed distal end 3170. The orifice 3172 may have a diameter between about 0.0508 mm (0.002 inches) and about 0.1016 mm (0.004 inches), or about 0.0787 mm (0.0031 inches). The inner diameter of the distal supply tube 3168 may be between about 0.3048 mm (0.012 inches) and about 0.4826 mm (0.019 inches), or between about 0.3556 mm (0.014 inches and about 0.4318 mm (0.017 inches) or about 0.3937 mm (0.0155 inches). The lumen 3176 of the distal supply tube 3168 is a continuation of an overall flow path emanating from a fluid source (e.g., saline bag, saline bottle) including an extension tubing (not shown). In some embodiments, the lumen 3176 of the distal supply tube 3168 may taper, for example, from an inner diameter of about 0.3937 mm (0.0155 inches) at a proximal portion to an inner diameter of about 0.2974 mm (0.011 inches) at a distal portion. In some embodiments, the equivalent of a taper may be achieved by bonding different diameter tubing to each other, resulting in a stepped-down tubing inner diameter. In some embodiments, different diameter tapered tubing may be bonded to each other, for a combination of tapering and step-down of diameter. An output pressure wave (for example, of saline injected via a pump) causes a liquid injectate to flow through the flow path, including a distal supply tube 3168 (arrow 3182), and causes a fluid jet 3178 to exit the orifice 3172 at a high velocity. The fluid jet 3178 serves to macerate thrombus 3164 that is sucked into the aspiration lumen 3160, and also can serve to dilute the thrombus. This maceration and dilution assures that there is continuous flow through the aspiration lumen 3160 so that it will not clog. The fluid jet 3178 is configured to be contained within the aspiration lumen 3160, and to not exit into a blood vessel or other body lumen. A guidewire tube 3132 having a distal end 3136 and a proximal end 3137 and having a distal port 3139 and a proximal port 3141 is secured to the aspiration catheter 3000 with attachment materials 3186. Though the guidewire tube 3132 of FIG. 34 is shown having a length that is shorter than the length of the aspiration catheter 3000 (sometimes referred to as a rapid exchange catheter), in other embodiments, the guidewire tube 3132 may extend substantially the entire length of the aspiration catheter 3000. In some embodiments, the aspiration catheter 3000 may have a length of between 100 cm and 180 cm, and the guidewire tube 3132 may have a length of 28 cm or less. In some embodiments, the guidewire tube 3132 may be a length of 25 cm or less. In some embodiments, the guidewire tube may have a length of 10 cm or less. In some embodiments the guidewire tube may have a length of 3 cm or less. In some embodiments, the guidewire tube may have a length of between about 3 cm and about 28 cm. The guidewire tube 3132 may be located adjacent (i.e., lateral) to the aspiration lumen 3160, or may be located co-axially within the aspiration lumen 3160. An additional guidewire 3102 may be used along with any aspiration catheter (including, for example, the aspiration catheter 3000) to facilitate the movement of aspirated or macerated thrombus through a catheter lumen, for example, through the aspiration lumen 3160 of the aspiration catheter 3000. The guidewire 3102 is secured at its proximal end 3188 (FIG. 37) to any of the embodiments of the guidewire manipulation device 100, 132, 140, 170, 190, 220, 2100, 650, 1100. A distal end 3143 may include a straight portion 3145 or a curved portion 3147, or a combination of a straight portion 3145 and a curved portion 3147. The guidewire 3102 may include a curved portion 3149 which is not located at the very distal end 3143. The curved portion 3147, 3149 may comprise a single arc or multiple arcs, but may generally comprise any non-straight pattern. The one or more arcs may be contained within a plane, or they may be three-dimensional. The curved portion 3147, 3149 may comprise a helix, such as a single diameter helix or a tapering diameter helix. The tapering diameter helix may taper such that the diameter increases as it extends distally, or such that the diameter decreases as it extends distally. In some cases, a fully straight guidewire 3102 may be used.

In FIG. 34, either the straight portion 3145 of the distal end 3143 or the curved portion 3147 of the distal end 3143 (or both in combination) may be placed adjacent or within the thrombus 3164 by inserting the guidewire 3102 through the aspiration lumen 3160 of the aspiration catheter 3000, and then operating the guidewire manipulation device 100, 132, 140, 170, 190, 220, 2100, 650, 1100 to rotate, longitudinally cycle, or otherwise move the guidewire 3102. The movement caused at the distal end 3143 of the guidewire 3102 serves to help to break up or macerate the thrombus 3164, and also help to move the partially or completely macerated thrombus 3164 (or a portion thereof) towards the aspiration catheter 3000 and particularly towards the open distal end 3158 of the aspiration lumen 3160 of the aspiration catheter 3000. The curved portion 3149 within the aspiration lumen 3160 of the aspiration catheter 3000 also serves to facilitate the movement of the partially or completely macerated thrombus 3164 (or a portion thereof) through the aspiration lumen 3160 of the aspiration catheter 3000, towards a proximal end of the aspiration lumen 3160. The curved portion 3149 may also serve to help center the guidewire 3102 within the aspiration lumen 3160 or to stabilize the guidewire 3102 as it is rotated or longitudinally moved by the guidewire manipulation device 100, 132, 140, 170, 190, 220, 2100, 650, 1100. In some cases, the guidewire 3102 may be slowly pulled proximally during the aspiration of the thrombus 3164, so that the curved portion 3149 helps to translate portions of thrombus. In some embodiments, the curved portion 3149 may be replaced by a straight portion. For example, a guidewire may comprise an outer coil extending along its longitudinal axis, which comprise external contours that will serve to macerate or translate a portion of thrombus. The guidewire manipulation device 100, 132, 140, 170, 190, 220, 2100, 650, 1100 may be operated such that the guidewire 3102 is rotated in a direction such that the curved portion 3149 (or the straight portion of helical coil) rotates in a direction that preferentially moves the portion of thrombus proximally in the aspiration lumen, in a similar action to an impeller or Archimedes screw. If the aspiration lumen 3160 of the aspiration catheter 3000 becomes clogged with thrombus or other embolus, the guidewire manipulation device 100, 132, 140, 170, 190, 220, 2100, 650, 1100 may be attached to a guidewire 3102 that is already in place (i.e., through a guidewire lumen) to guide the catheter, and then the guidewire manipulation device may be activated to move (rotate, longitudinally translate, etc.) the guidewire 3102 to help dislodge the thrombus or other embolus so that it can be fully aspirated/evacuated and removed from the aspiration lumen 3160, thus eliminating the clog. The guidewire 3102 or other elongate medical devices may be fabricated from a number of different biocompatible materials, including, but not limited to stainless steels or shape-memory alloys such as nickel-titanium alloys (Nitinol).

Figure 35:
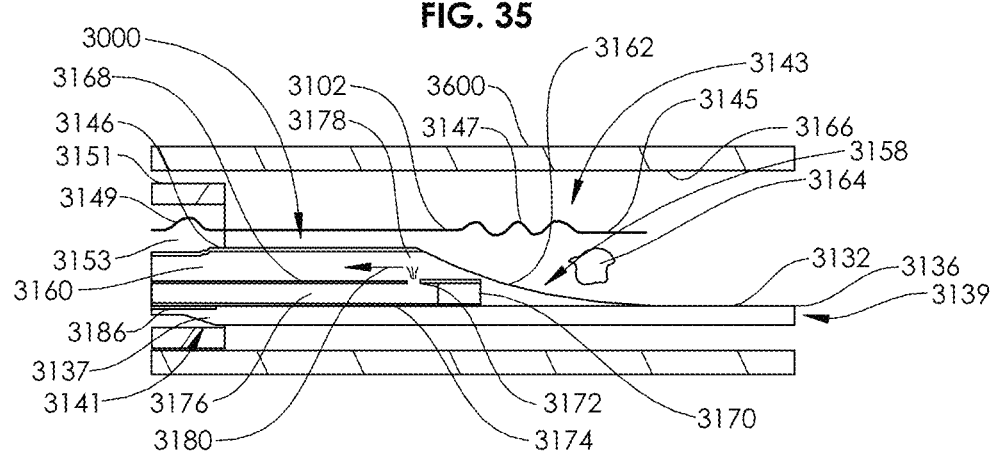
FIG. 35 illustrates an aspiration catheter within a blood vessel being used in conjunction with a guidewire which is moved by a guidewire manipulation device, according to another embodiment of the present disclosure.

In FIG. 34, both the aspiration catheter 3000 and the guidewire 3102 may be inserted (separately or together) through a delivery catheter, such as a coronary guiding catheter. FIG. 35 illustrates the aspiration catheter 3000 and a guidewire 3102 inserted through a delivery catheter 3151, such as a coronary guiding catheter, but in this case, the guidewire 3102 is radially adjacent the aspiration catheter, within an annulus between the interior of the delivery catheter 3151 and the exterior of the aspiration catheter 3000. Thus, the guidewire 3102 may be moved or manipulated by the guidewire manipulation device 100, 132, 140, 170, 190, 220, 2100, 650, 1100 such that the distal end 3143 aids the maceration or movement of the thrombus 3164 not only into the aspiration lumen 3160 of the aspiration catheter 3000, but also into the lumen 3153 of the delivery catheter 3151. The curved portion 3149 (or a straight portion) is configured to aid the movement of the thrombus 3164 (or a portion thereof) through the lumen 3153 of the delivery catheter 3151. In some cases, the guidewire 3102 may be slowly pulled proximally during the aspiration of the thrombus 3164, so that the curved portion 3149 helps to translate portions of thrombus 3164. In other embodiments, two guidewires 3102 and two guidewire manipulation devices 100, 132, 140, 170, 190, 220, 2100, 650, 1100 may be used, in a combination of the methods of FIG. 34 and FIG. 35. The aspiration catheters described herein may include any standard aspiration catheter having one or more aspiration lumens. Aspiration catheters used herein may include the ACE™ or INDIGO® catheters produced by Penumbra, Inc. of Alameda, Calif., USA.

Aspiration catheters and aspiration systems may include those described in U.S. Patent Application Publication No. 2015/0282821 to Look et al., published Oct. 8, 2015, which is incorporated herein by reference in its entirety for all purposes.

Aspiration catheters and aspiration systems may include those described in U.S. Patent Application Publication No. 2015/0327875 to Look et al., published Nov. 19, 2015, which is incorporated herein by reference in its entirety for all purposes.

Figure 38:
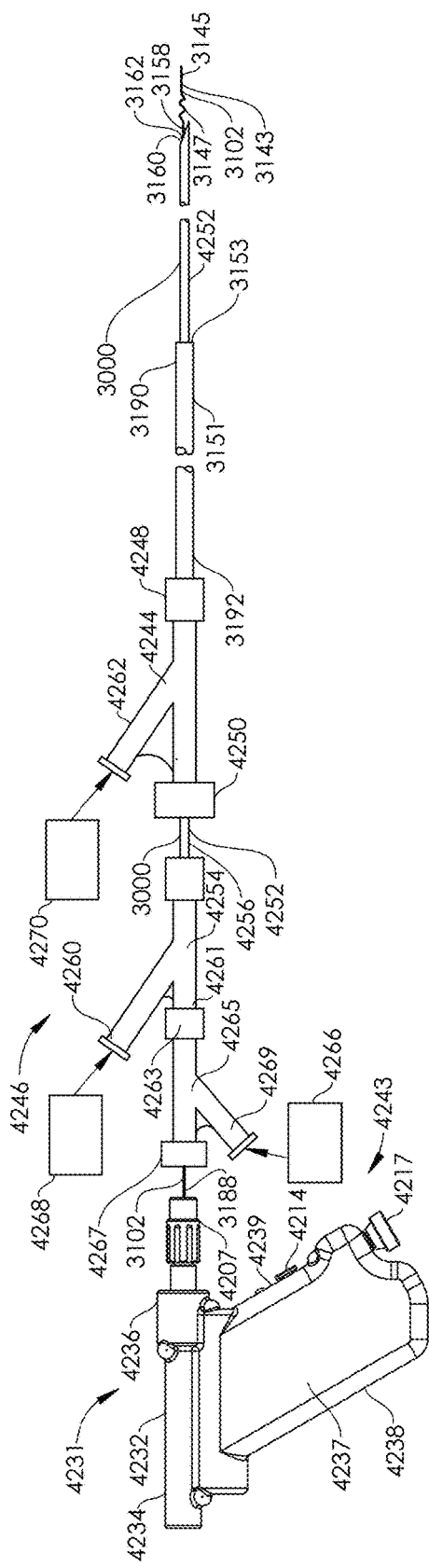
FIG. 38 illustrates a plan view of a system for treating a patient having thrombus, according to an embodiment of the present disclosure.

FIG. 38 illustrates a system for treating thrombus 4246. The system for treating thrombus 4246 includes a delivery catheter 3151 having a lumen 3153 through which an aspiration catheter 3000 is placed. A guidewire 3102 may be inserted either through the lumen 3153 of the delivery catheter 3151, or (as shown in FIG. 38) through a lumen of the aspiration catheter 3000, for example, through the aspiration lumen 3160 of the aspiration catheter 3000. The guidewire 3102 is configured to be manipulated (rotationally and/or longitudinally) by a guidewire manipulation device 4231 having a housing 4232 and a handle 4237. The guidewire manipulation device 4231 may include any of the embodiments described herein, or may include embodiments of guidewire manipulation devices such as those disclosed in co-pending U.S. patent application Ser. No. 15/235,920, filed on Aug. 12, 2016 and entitled "System and Method for Manipulating an Elongate Medical Device," which is incorporated by reference herein in its entirety for all purposes. The delivery catheter 3151 has a proximal end 3192 and a distal end 3190, with the proximal end 3192 coupled to a y-connector 4244 by a luer connection 4248. The luer connection 4248 may include in some embodiments a female luer attached to the proximal end 3192 of the delivery catheter 3151 and a male luer at the distal end of the y-connector 4244. A hemostasis valve 4250 at the proximal end of the y-connector 4244 is configured to seal around a shaft 4252 of the aspiration catheter 3000, and may include a Touhy-Borst, a spring-loaded seal, a duckbill seal, or other seals. A connector 4254 is attached to the proximal end 4256 of the aspiration catheter 3000. The connector 4254 includes a central bore 4258 which is in fluid communication with the aspiration lumen 3160, and which terminates in a connector 4261 (for example, a female luer connector). In embodiments wherein the aspiration catheter 3000 comprises a forced aspiration catheter, a port 4260 is in fluid communication with the lumen 3176 of the distal supply tube 3168 (FIG. 34). Thus the port 4260 may be configured to be coupled to a source of pressurized fluid 4268 (e.g., normal saline). The connector 4261 is configured to be coupled to a connector 4263 at the distal end of a y-connector 4265. The connector 4263 may comprise a male luer. The y-connector 4265 includes a hemostasis valve 4267 (Touhy-Borst, spring-loaded seal, etc.) and a sideport 4269. The hemostasis valve 4267 is configured to seal around the guidewire 3102. The sideport 4269 of the y-connector 4265 is configured to be coupled to a vacuum source 4266. The sideport 4262 of y-connector 4244 may additionally be configured to be coupled to a vacuum source 4270, and/or may be used for injections of fluids, such as contrast media.

The aspiration catheter 3000 includes an open distal end 3158, which may include a skive 3162. The guidewire 3102 is shown in FIG. 38 having a distal end 3143 which includes a curved portion 3147 and a straight portion 3145, though other distal configurations are also contemplated, including curved only or straight only. The guidewire 3102 is shown extending through the aspiration lumen 3160 of the aspiration catheter 3000 and proximally through the connector 4254 and through the y-connector 4265. The guidewire 3102 may be secured at its proximal end 3188 to a rotatable chuck 4207, which is rotatably carried by the guidewire manipulation device 4231. The chuck 4207 may be manipulated to selectively grip and ungrip (engage and unengage, lock and unlock, etc.) the guidewire 3102 via a collet, or any equivalent means. The guidewire manipulation device 4231 is configured to be supported by the hand of a user, and includes the handle 4237 which has one or more controls 4243. The handle 4237 may extend in a generally perpendicular direction from the axis of the guidewire 3102 as it extends through the housing 4262, and may angle towards a distal end 4236 of the housing 4232 (as shown in FIG. 38) in a reverse gun handle grip. Alternatively, the handle 4237 may have a standard gun handle grip (see FIG. 37), and thus may angle towards a proximal end 4234 of the housing 4232. The controls 4243 are shown in FIG. 38 carried on a distally-facing surface 4239 of the handle 4237, and may be configured in this embodiment to be operated by one or more finger of the hand of the user, which may include non-thumb fingers. The controls 4243 may include an activation button 4214 which is configured to turn power on an off, for example, to power a motor (not shown) which is configured to rotate and/or longitudinally move the guidewire 3102. A control knob 4217 may be configured to increase or decrease a rotation speed (e.g., of the motor) or to select a plurality of different manipulation routines. The manipulation routines may be stored within memory that is carried within the guidewire manipulation device 4231, for example, on a circuit board. The circuit board may include a controller, as described in relation to the other embodiments herein. An exemplary manipulation routine may include rotating the guidewire 3102 in a first rotational direction eight rotations, and then rotating the guidewire 3102 in a second, opposite, rotational direction eight rotations. Another manipulation routine may include rotating continuously in a single direction. Another manipulation routine may include rotating continuously in one direction while repeatedly translating the guidewire 3102 distally and proximally (longitudinal cycling). Alternatively, the controls 4243 may be carried on a proximally-facing surface 4238 of the handle 4237, and may be configured to be operated primarily by the thumb of the hand of the user. The motor may be connected to the chuck 4207 directly, or by other drive elements, including gearing, which may be used to change speeds, torques, or rotational directions. The drive elements may include those described in relation to any of the embodiments disclosed herein. In use, the vacuum source 4266 may be coupled to the sideport 4269 of the y-connector 4265, and thrombus may thus be aspirated through the aspiration lumen 3160 of the aspiration catheter 3000. The vacuum source 4266 may comprise a syringe, a vacuum chamber, or a vacuum pump. Syringes with lockable plungers, for example syringes having volumes of between about 20 ml and about 30 ml, may be used as the vacuum source. While performing an aspiration procedure, the user may simultaneously or sequentially operate the guidewire manipulation device 4231 to rotate and/or longitudinally move the guidewire 3102, in order to aid the maceration of the thrombus and/or the movement of the thrombus or pieces of the thrombus through the aspiration lumen 3160.

Figure 37:
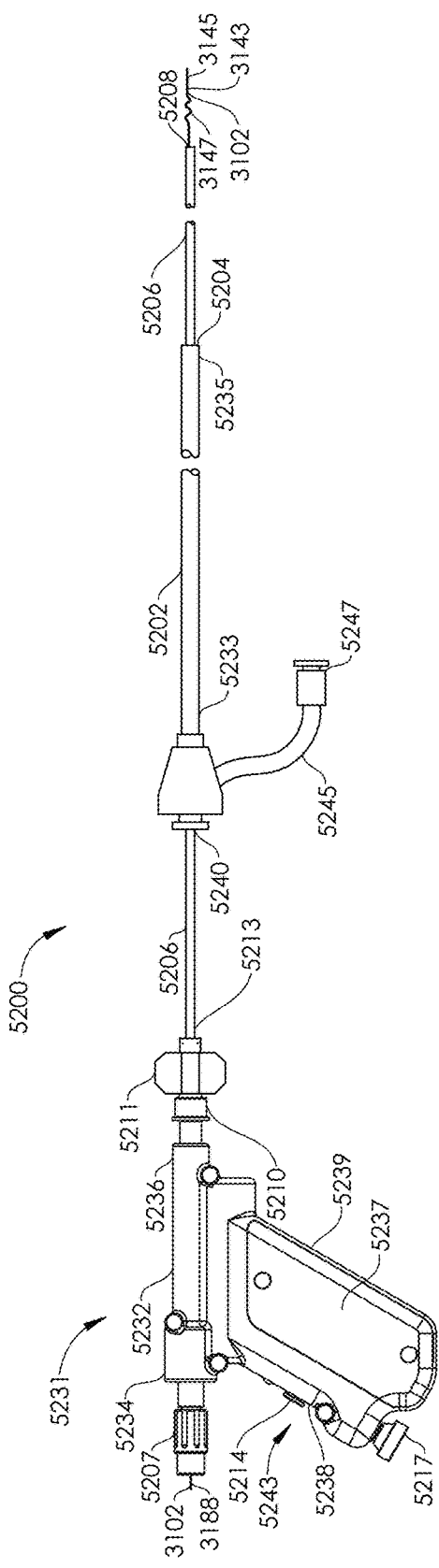
FIG. 37 illustrates a plan view of a system for treating a patient having thrombus, according to an embodiment of the present disclosure.

FIG. 37 illustrates a system for treating thrombus 5200. The system for treating thrombus 5200 includes a sheath 5202 having a lumen 5204 passing therethrough through which a microcatheter 5206 is placed. A guidewire 3102 may be inserted a lumen 5208 of the microcatheter 5206. The guidewire 3102 is configured to be manipulated (rotationally and/or longitudinally) by a guidewire manipulation device 5231 having a housing 5232 and a handle 5237. The guidewire manipulation device 5231 may include any of the embodiments described herein, or may include embodiments of guidewire manipulation devices such as those disclosed in co-pending U.S. patent application Ser. No. 15/235,920, filed on Aug. 12, 2016 and entitled "System and Method for Manipulating an Elongate Medical Device." The housing 5232 has a proximal end 5234 and a distal end 5236 and the handle 5237 extends in a substantially radial direction from the guidewire axis of the housing 5232. Controls 5243 are carried by a proximally-facing surface 5238, and include an activation button 5214 and a control knob 5217, which may be configured similar to the activation button 4214 and the control knob 4217 of the guidewire manipulation device 4231 of the embodiment of FIG. 38. The user's hand is configured to grip the standard gun handle grip of the handle 5237 by wrapping around the distally-facing surface 5239. The handle 5237 is depicted in FIG. 37 angling toward the proximal end 5234 of the housing 5232. The user may operate the controls 5243 using the user's thumb, or a combination of the user's thumb and one of the non-thumb fingers of the user's hand. A chuck 5207 is carried by the guidewire manipulation device 5231 adjacent the proximal end 5234 of the housing 5232 and is configured to rotate and/or longitudinally move the guidewire 3102 in a similar manner to the chuck 4207 of FIG. 38. However, the guidewire 3102 is configured to pass through the housing 5232 and a proximal end 3188 of the guidewire 3102 is configured to be secured to the chuck 5207. The guidewire manipulation device 4231 includes a locking element 5210 carried adjacent the distal end 5236 of the housing 5232 which is connectable to a connector 5211 which is coupled to a proximal end 5213 of the microcatheter 5206. The locking element 5210 and the connector 5211 comprise male and female luer locks, or may comprise other types of locking connections which secure the connector 5211 with respect to the guidewire manipulation device 5231. When the locking element 5210 and the connector 5211 are secured to each other, relative rotational and/or longitudinal motion between the guidewire manipulation device 5231 and the connector 5211 are inhibited. The sheath 5202 includes a proximal end 5233 and a distal end 5235, and may include a proximal internal seal 5241, and a sideport 5245 having a luer 5247. In use, the user may operate the guidewire manipulation device 5231 (for example, by holding the handle 5237 and pressing the activation button 5214) while also moving pushing or pulling the microcatheter 5206 within the lumen 5204 of the sheath 5202. Thrombus may be macerated by the distal end 3143 of the guidewire 3102. If desired, the thrombus may be aspirated through the lumen 5204 of the sheath 5202, by applying a vacuum (e.g., attaching a vacuum source, not shown) to the sideport 5245 of the sheath 5202. The sheath 5202 may also be moved proximally or distally so that the distal end 5235 of the sheath approaches the thrombus or portions of thrombus or blood to be aspirated. If desired, the locking element 5210 of the guidewire manipulation device 5231 may be detached from the connector 5211 of the microcatheter 5206, and a vacuum source (not shown) may be attached to the connector 5211 in order to aspirate thrombus or blood through the lumen 5208 of the microcatheter 5206.

Figure 36:
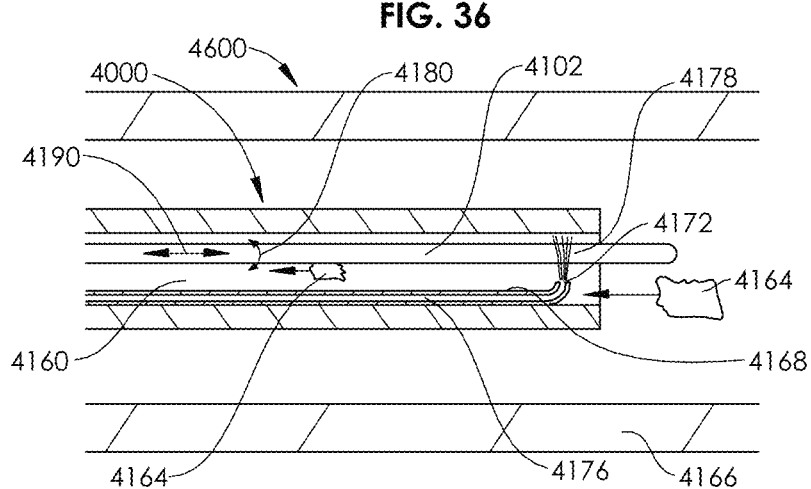
FIG. 36 illustrates an aspiration catheter within a blood vessel used in conjunction with a guidewire which is moved by a guidewire manipulation device, according to another embodiment of the present disclosure.

FIG. 36 illustrates an aspiration catheter 4000 within a blood vessel 4600 having a blood vessel wall 4166. The aspiration catheter 4000 has an aspiration lumen 4160 which is configured for aspirating thrombus 4164 and also for placement of a guidewire 4102 which is configured to track the aspiration catheter 4000 through the vasculature of a patient. A distal supply tube 4168 having a lumen 4176 is configured for injecting pressurized fluid, such as saline. The pressurized fluid is injected through the lumen 4176 and out an orifice 4172 into the aspiration lumen 4160. The orifice is located at the extreme distal end of the distal supply tube 4168. The output of the pressurized fluid through the orifice 4172 may comprise a jet 4178. Thrombus 4164 is aspirated into the aspiration lumen 4160. In some embodiments, the jet 4178 macerates the thrombus 4164 as it passes by the jet 4178. The guidewire 4102 may be attached to the guidewire manipulation device 100, 132, 140, 170, 190, 220, 2100, 650, 1100, 4231 and moved by the guidewire manipulation device 100, 132, 140, 170, 190, 220, 2100, 650, 1100, 4231 in one or more patterns including rotation motion 4180 and/or longitudinal motion 4190. Either or both of these motions may be imparted on the guidewire 4102 to conjunctively aid the maceration of the thrombus 4164, and/or to aid in the transport of the thrombus 4164 from distal to proximal through the aspiration lumen 4160. The rotational motion 4180 may include clockwise only, counter-clockwise only, or a combination of clockwise and counter-clockwise, for example back and forth rotational oscillation as described herein. The longitudinal motion 4190 may be movement imparted directly on the guidewire 4102 by the operation of the guidewire manipulation device 100, 132, 140, 170, 190, 220, 2100, 650, 1100, 4231, or may be manually applied by the user by moving the guidewire manipulation device 100, 132, 140, 170, 190, 220, 2100, 650, 1100, 4231 back and forth (distally and proximally). In some cases, the guidewire manipulation device 100, 132, 140, 170, 190, 220, 2100, 650, 1100, 4231 may be gradually pulled while the guidewire 4102 is rotated by the guidewire manipulation device 100, 132, 140, 170, 190, 220, 2100, 650, 1100, 4231. In some cases, the handle of the guidewire manipulation device can be cyclically moved distally and proximally while generally pulling the guidewire manipulation device 100, 132, 140, 170, 190, 220, 2100, 650, 1100, 4231 proximally. For example, one cm distally, two cm proximally, one cm distally, two cm proximally, etc. In some embodiments, the aspiration catheter 4000 may consist only of a single lumen for aspiration and guidewire placement, without any forced injection (i.e., no distal supply tube 4168). In some embodiments, the manipulation of the guidewire 4102 by the guidewire manipulation device 100, 132, 140, 170, 190, 220, 2100, 650, 1100, 4231 performs a similar function to a "separator device" as is used with the ACE™ or INDIGO® aspiration catheters produced by Penumbra, Inc. of Alameda, Calif., USA. The "separator device" is a guidewire type device with a ball or football-shaped portion at its tip that extends from an aspiration lumen and is pulled against the distal port of the aspiration lumen to help disrupt or macerate the thrombus/clot.

A variety of different elongate medical devices may be rotated, longitudinally moved, or otherwise manipulated by the embodiments of the guidewire manipulation device 100, 132, 140, 170, 190, 220, 2100, 650, 1100, 4231 described herein, including embodiments of the elongated medical instrument and the macerator which are disclosed in U.S. Patent Application Publication No. 2014/0142594 to Fojtik, published May 22, 2014, which is incorporated herein by reference in its entirety for all purposes.

In one embodiment a manipulation device includes a housing configured to be supported by the hand of a user, the housing having a distal end and a proximal end, a drive system disposed within the housing and configured to rotate a rotation member, an engagement member coupled to the rotation member and configured to be remotely coupled to an elongate medical device to transfer rotational movement of the rotation member to rotational movement of an elongate medical device, an activation member carried by the housing such that the activation member can be operated by at least a portion of the hand of the user when the housing is supported by the hand of the user, and wherein the drive system is configured to apply a combination of motive force components to the engagement member. In some embodiments, the combination of motive force components includes an alternating clockwise motion and counter-clockwise motion. In some embodiments, the combination of motive force components comprises a rotational motion and a cyclic longitudinal motion. In some embodiments, the activation member comprises a handle coupled to the housing and configured to be operable by the hand of the user. In some embodiments, the handle is configured to couple to the drive system mechanically. In some embodiments, the rotation member includes a tube having a window. In some embodiments, the manipulation device further includes a motor operatively coupled to the drive system, wherein the activation member is configured to initiate operation of the motor. In some embodiments, the manipulation device further includes gearing coupled to the motor. In some embodiments, the activation member includes a switch. In some embodiments, the elongate medical device consists of at least one of a guidewire, a basket, an expandable device, a catheter shaft, a macerator, or a cutting device. In some embodiments, the combination of motive force components comprises a helical motion. In some embodiments, the combination of motive force components comprises a jackhammer motion.

In another embodiment, a method for treating a patient having thrombus comprises providing a manipulation device comprising a housing configured to be supported by the hand of a user, the housing having a distal end and a proximal end, a drive system disposed within the housing and configured to rotate a rotation member, an engagement member coupled to the rotation member, and configured to be removably coupled to an elongate medical device, an activation member carried by the housing such that it can be operated by at least a portion of the hand of the user when the housing is supported by the hand of the user, and wherein the drive system is configured to apply motive force to the engagement member, securing an elongate member to the engagement member, the elongate member having a distal end configured for introduction into a patient's vasculature, introducing at least the distal end of the elongate member into a blood vessel adjacent a thrombus, operating the activation member to cause at least some rotation of the rotation member, which in turn causes at least some rotation of the distal end of the elongate member at or near the thrombus, and aspirating at least some thrombus with an aspiration catheter. In some embodiments, the motive force comprises a combination of motive force components including an alternating clockwise motion and counterclockwise motion. In some embodiments, the combination of motive force components comprises a rotational motion and a cyclic longitudinal motion. In some embodiments, the activation member comprises a handle coupled to the housing and configured to be operable by the hand of the user. In some embodiments, the handle is configured to couple to the drive system mechanically. In some embodiments, the rotation member comprises a tube including a window. In some embodiments, the manipulation device further comprises a motor operatively coupled to the drive system, wherein the activation member is configured to initiate operation of the motor. In some embodiments, the manipulation device further comprises gearing coupled to the motor. In some embodiments, the activation member comprises a switch. In some embodiments, the elongate medical device consists of at least one of a guidewire, a basket, an expandable device, a catheter shaft, a macerator, and a cutting device. In some embodiments, the combination of motive force components comprises a helical motion. In some embodiments, the combination of motive force components comprises a jackhammer motion. In some embodiments, the elongate member comprises a guidewire. In some embodiments, the distal end of the elongate member is substantially straight. In some embodiments, the distal end of the elongate member is curved. In some embodiments, at least a portion of the aspiration catheter extends alongside at least a portion of the elongate member within a delivery lumen of a delivery catheter. In some embodiments, the at least some rotation of the distal end of the elongate member facilitates movement of the thrombus through the delivery lumen of the delivery catheter. In some embodiments, the delivery catheter is a coronary guiding catheter. In some embodiments, the elongate member extends within a lumen of the aspiration catheter. In some embodiments, the elongate member extends within an aspiration lumen of the aspiration catheter. In some embodiments, the elongate member is rotatable within the lumen of the aspiration catheter. In some embodiments, the at least some rotation of the distal end of the elongate member facilitates movement of the thrombus through the lumen of the aspiration catheter. In some embodiments, the aspiration catheter comprises a supply lumen and an aspiration lumen, the supply lumen having a wall and a closed distal end, the aspiration lumen configured to couple to a vacuum source and having an interior wall surface and an open distal end, the wall of the supply lumen having an orifice in fluid communication with the interior of the aspiration lumen, the orifice located proximally of the open end of the aspiration lumen and adjacent the closed distal end of the supply lumen. In some embodiments, the method further comprises providing a tubing set having a first conduit configured to couple the supply lumen of the aspiration catheter to a fluid source, and a pump component associated with the first conduit and configured to detachably couple to a drive unit, such that the motion from the drive unit is transferred to the pump component such that resultant motion of the pump component causes fluid from the fluid source to be injected through the supply lumen of the aspiration catheter, and through the orifice into the aspiration lumen. In some embodiments, the pump comprises a piston. In some embodiments, the orifice is configured to create a spray pattern when pressurized fluid is pumped through the supply lumen such that the spray pattern impinges on the interior wall surface of the aspiration lumen. In some embodiments, the aspiration catheter comprises a tubular aspiration member having a proximal end, a distal end, and a lumen, and configured to at least partially extend out of the lumen of a delivery catheter having a lumen, and into the vasculature of a subject, an elongate support member coupled to the tubular aspiration member and extending between a proximal end of the aspiration catheter and the proximal end of the tubular aspiration member, and an annular seal comprising at least one annular sealing member coupled to the tubular aspiration member.

In another embodiment, a method for breaking up a thrombus or embolus comprises providing a manually-operated guidewire manipulation device comprising a housing having a proximal end, an elongate body, and a distal end, a rotation member disposed within the housing and configured to rotate with respect to the housing, a locking assembly operably coupled to a distal end of the rotation member, the locking assembly having a locked mode wherein the rotation member is engaged with the guidewire, and an unlocked mode wherein the rotation member is disengaged from the guidewire, a handle coupled to the housing and configured to be operable by one hand of a user, and a drive system operably coupled to the handle, the drive system configured to rotate the rotation member upon actuation of the handle by the one hand of the user in a first direction with respect to the housing, thereby causing the guidewire to rotate in a first rotational direction when the locking assembly is in the locked mode, wherein the handle is configured to be releasable by the user such that the handle when released moves in a second direction with respect to the housing, the second direction opposite from the first direction, wherein the handle is configured to cause rotation of the rotation member in a second rotational direction opposite the first rotational direction when the handle moves in the second direction, thereby causing the guidewire to rotate in the second rotational direction, securing a guidewire to the rotation member via the locking assembly, the guidewire having a distal end extending through the lumen of a catheter and into a patient's vasculature, operating the manually-operated guidewire manipulation device to cause at least some rotation of the rotation member, which in turn causes at least some rotation of the guidewire, and aspirating at least some thrombus or embolus through the lumen of the catheter. In some embodiments, the catheter is an aspiration catheter. In some embodiments, the lumen is an aspiration lumen. In some embodiments, the aspiration lumen is also a guidewire lumen. In some embodiments, the catheter is a guiding catheter.

In some embodiments described herein, instead of a chuck being rotated, luer lock connector may instead be rotated. For example, a rotatable male luer lock connector may be coupled to a medical device (such as an elongated medical device, which may include a catheter), in order to rotated the medical device.

In some embodiments, the medical device to be rotated, axially displaced or moved in any other pattern may comprise one or more of: a drill bit, a burr, for example, burr systems for specialized Craniotomy use. In some embodiments, the system may include a safety stop. In some embodiments, the medical device to be rotated, axially displaced or moved in any other pattern may comprise one or more of: a tapered tip device that is advanced by spinning (for example a skived catheter), cutting tools for bone work, gigli saw wires, hollow trephines for biopsy (flexible or rigid), dissecting elements that slide or find channels (and may in some cases be able to expand), retriever expanding stent-like structures to penetrate thrombus and subsequently expand once in place, balloon like or other expandable structures that deliver drugs by rubbing against a vessel wall either by axial motion, rotation or a combination. It can be appreciated that by connection to any of the embodiments described herein, medical devices of a variety of types may be manipulated into motion such as rotating (one or more rotational directions), and pecking (forward and back). Additionally, oscillating action may be used in a coaxial system to move two elements in relation to each other, to release particles, drugs, or other materials. In some embodiments, the medical device to be rotated, axially displaced or moved in any other pattern may comprise one or more of: an endoscopic trocar introducer, via wire, a Veress needle introducer, a female uterine cervix fallopian tube traversing device for i.e. sterility device implantation, a ureter traversing for i.e. kidney stone manipulation, a filing system for root canals, a FESS (functional endoscopic sinus surgery) or burr-like surgical device, a sinusoidal/nasal access, a plastic surgery device for tunneling under layers of skin dermis, fat, a neurosurgical nose access device, a deep brain access device, for example a University of Pennsylvania Deep Brain Stimulation (DBS) device. In some embodiments, the medical device to be rotated, axially displaced or moved in any other pattern may comprise one or more of: a hollow fenestrated wire drug delivery which delivers drugs while spinning, drugs such as G2B3 Inhibitors which may be delivered at or into thrombus. In some embodiments, the medical device to be rotated, axially displaced or moved in any other pattern may comprise one or more of: an aneurysmal wire/catheter navigation and liquid embolic dispensing device.

While the foregoing is directed to embodiments of the present disclosure, other and further embodiments may be devised without departing from the basic scope thereof.

What is claimed is:

1. A system for treating a patient having thrombus, comprising:
    an aspiration catheter having a distal end for placement into a blood vessel, a proximal end, and an aspiration lumen extending between the distal end and the proximal end and configured to be coupled to a vacuum source, the aspiration lumen configured for aspirating thrombus therethrough;
    an elongate member having a distal end and a proximal end, the distal end having a straight distal portion such that the elongate member is configured to be inserted through the aspiration lumen of the aspiration catheter such that the distal end extends from the aspiration lumen into a thrombus within the blood vessel;
    a manipulation device comprising:
        a housing configured to be supported by the hand of a user, the housing having a distal end and a proximal end;
        a drive system disposed within the housing, and configured to rotate a rotation member;
        an engagement member coupled to the rotation member, and configured to be releasably coupled to the elongate member to transfer rotational movement of the rotation member to rotational movement of the elongate member;
        an activation member carried by the housing such that it can be operated by at least a portion of the hand of the user when the housing is supported by the hand of the user; and
    wherein the drive system is configured to apply motive force to the engagement member to thereby move the elongate member, wherein the motive force comprises a combination of motive force components comprising an alternating clockwise motion and counter-clockwise motion.

2. The system of claim 1, wherein the motive force comprises a combination of motive force components comprising a rotational motion and a cyclic longitudinal motion.

3. The system of claim 1, wherein the elongate member comprises a guidewire.

4. The system of claim 1, wherein the distal end of the elongate member consists of the straight distal portion.

5. The system of claim 1, wherein the distal end of the elongate member further comprises a curved portion proximal to the straight distal portion.

6. The system of claim 1, further comprising a delivery catheter having a proximal end, a distal end, and a delivery lumen extending between the proximal end and the distal end of the delivery catheter, the delivery lumen configured to allow simultaneous placement of the aspiration catheter and the elongate member therein.

7. The system of claim 6, wherein the delivery catheter comprises a coronary guiding catheter.

8. The system of claim 1, wherein the elongate member comprises an expandable device.

9. The system of claim 1, wherein the elongate member comprises a catheter shaft.

10. The system of claim 1, wherein the elongate member comprises a macerator.

11. The system of claim 1, wherein the motive force comprises a helical motion.

12. The system of claim 1, wherein the motive force comprises a jackhammer motion.

13. The system of claim 1, wherein the elongate member, when rotated, is configured to facilitate movement of at least some thrombus through the aspiration lumen of the aspiration catheter.

14. The system of claim 1, wherein the aspiration catheter further comprises a distal supply tube having a proximal end configured to be coupled to a fluid source, a distal portion having an orifice, and a lumen, the distal supply tube extending within the aspiration lumen, and the orifice configured to allow fluid injected through the lumen of the distal supply tube to enter the aspiration lumen as a jet.

15. The system of claim 14, wherein the orifice is at an open distal end of the distal supply tube.

16. The system of claim 14, wherein a distal end of the distal supply tube is closed, and wherein the orifice is through a wall of the distal supply tube, adjacent to the closed distal end.

17. The system of claim 1, wherein the elongate member includes a first portion configured to reside within the aspiration lumen and to facilitate the movement of partially or completely macerated thrombus through the aspiration lumen while the elongate member is moved in relation to the aspiration catheter.

18. The system of claim 17, wherein the first portion of the elongate member is configured to help center or stabilize the elongate member within the aspiration lumen.

19. The system of claim 1, therein the engagement member comprises a chuck having a collet configured to directly grip the elongate member.

* * * * *